United States Patent
Kaufmann et al.

(10) Patent No.: US 8,475,410 B2
(45) Date of Patent: Jul. 2, 2013

(54) EXTERNALLY TRIGGERABLE CANNULA ASSEMBLY

(75) Inventors: Heiner Kaufmann, Bern (CH); Simon Scheuer, Bern (CH); David Teutsch, Schuepfen (CH)

(73) Assignee: Roche Diagnostics International AG, Steinhausen (CH)

( * ) Notice: Subject to any disclaimer, the term of this patent is extended or adjusted under 35 U.S.C. 154(b) by 217 days.

(21) Appl. No.: 12/951,151

(22) Filed: Nov. 22, 2010

(65) Prior Publication Data
US 2011/0295205 A1 Dec. 1, 2011

(30) Foreign Application Priority Data
Nov. 26, 2009 (EP) ..................................... 09177194

(51) Int. Cl.
*A61B 17/34* (2006.01)
(52) U.S. Cl.
USPC ................. 604/136; 604/164.01; 604/164.07; 604/164.12; 604/157; 604/264
(58) Field of Classification Search
USPC .................... 604/164.01, 264, 272, 195, 131, 604/134–137, 156–157, 164.07, 164.12
See application file for complete search history.

(56) References Cited

U.S. PATENT DOCUMENTS

| 7,318,816 | B2 | 1/2008 | Bobroff et al. |
| 7,455,663 | B2 | 11/2008 | Bikovsky |
| 2004/0158207 | A1* | 8/2004 | Hunn et al. ............... 604/164.01 |
| 2006/0095014 | A1 | 5/2006 | Ethelfeld |
| 2007/0093754 | A1* | 4/2007 | Mogensen et al. ........ 604/164.01 |
| 2007/0142776 | A9 | 6/2007 | Kovelman et al. |
| 2007/0219597 | A1 | 9/2007 | Kamen et al. |
| 2008/0215035 | A1 | 9/2008 | Yodfat et al. |
| 2008/0249472 | A1 | 10/2008 | Liniger et al. |
| 2008/0249473 | A1 | 10/2008 | Rutti et al. |
| 2008/0319414 | A1 | 12/2008 | Yodfat et al. |
| 2009/0124979 | A1* | 5/2009 | Raymond et al. ............. 604/195 |
| 2009/0198191 | A1 | 8/2009 | Chong et al. |
| 2009/0198215 | A1 | 8/2009 | Chong et al. |

FOREIGN PATENT DOCUMENTS

| EP | 1764125 A1 | 3/2007 |
| EP | 1970084 A1 | 9/2008 |

(Continued)

OTHER PUBLICATIONS

Partial European Search Report, completed Jun. 15, 2010 for European Application No. EP 09177194, pp. 1-8.

*Primary Examiner* — Quynh-Nhu H Vu
(74) *Attorney, Agent, or Firm* — Dinsmore & Shohl LLP

(57) ABSTRACT

According to one embodiment, a cannula assembly may include a cannula module and an inserter module. In the pre-operational state the cannula is retracted with respect to the skin-contacting surface. In operational state the cannula projects beyond the skin-contacting surface. The inserter module may include an energy store and an activation mechanism. When the energy store is at least partially discharged, the stored potential energy is transformed to kinetic energy that moves the cannula from the pre-operational state to the operational state. The activation mechanism is triggerable from outside the cannula assembly with a trigger device. The activation mechanism prevents the energy store from being discharged before it is triggered by the trigger device, and enables the energy store to be discharge after it is triggered by the trigger device to force the cannula from the pre-operational state into the operational state.

7 Claims, 16 Drawing Sheets

FOREIGN PATENT DOCUMENTS

| | | |
|---|---|---|
| WO | 02081012 A2 | 10/2002 |
| WO | 2008098246 A1 | 8/2008 |
| WO | 2009004026 A1 | 1/2009 |
| WO | 2009010396 A1 | 1/2009 |
| WO | 2009016638 A1 | 2/2009 |
| WO | 2009033032 A1 | 3/2009 |
| WO | 2009039013 A1 | 3/2009 |
| WO | 2009050584 A2 | 4/2009 |

* cited by examiner

EXTERNALLY TRIGGERABLE CANNULA ASSEMBLY

CROSS REFERENCE TO RELATED APPLICATIONS

The present application claims priority to European Patent Application No. EP09177194 filed Nov. 26, 2009.

TECHNICAL FIELD

The embodiments described herein relate to methods, assemblies, systems and devices for administering a fluid or liquid such as a medical product or liquid insulin. More particularly, the embodiments described herein relate to methods, assemblies, systems and devices for administering a fluid or liquid via an externally triggerable cannula.

BACKGROUND

A fluid product may be continuously delivered to a body using a cannula that is inserted into the body and remains in place for a period of time such as, for example, several days. Diabetes patients may use a subcutaneously positioned cannula for a continuous delivery of insulin via a drug infusion pump or for monitoring glucose levels using a sensor. Frequently, the patient initially applies a subcutaneous insertion device which includes a cannula device for subsequently delivering insulin by means of the pump. Older and/or weakened patients may encounter difficulties in correctly administering the drug due to impaired manual dexterity or lack of motor skills needed to properly handle the cannula device. Such difficulties may give rise to a risk that an incorrect dose is administered or that the cannula device is unintentionally and/or inappropriately triggered.

The subcutaneous insertion device may be a separate, reusable device. However the use of such an additional device may be perceived as being complicated to handle. Alternatively, disposable insertion devices are available. Disposable insertion devices are supplied with an attached infusion cannula. Once insertion is complete, the insertion device can be removed from the cannula and disposed.

The use of disposable insertion devices may be more expensive compared to reusable devices due to an increase in consumption of disposable insertion devices and an increased volume of sterile packing for each infusion set.

US 2007/0142776 A9 discloses an insertion device and insertion set. The insertion device for inserting at least a portion of at least one piercing member of an insertion set through the skin of a patient includes a device housing, a carrier body and a driver. The carrier body is slidably received within the device housing for movement between an advanced position and a retracted position. The driver is operatively coupled between the device housing and the carrier body to urge the carrier body from the retracted position toward the advanced position to place at least a portion of the at least one piercing member of the insertion set thorough the skin of the patient to install the insertion set to the patient. The receiving structure of the carrier body is removable from the insertion set while maintaining the installation of the insertion set to the patient.

US 2008/0319414 A1 discloses an insertion apparatus and a method for use with a device for delivery of a therapeutic fluid into a body of a patient and/or for sensing of a bodily analyte. The apparatus includes a housing adapted for loading therein at least one cannula cartridge unit having a protective member. The protective member accommodates at least one penetrating cartridge having a subcutaneously insertable element and a penetrating member. The apparatus includes a displacement mechanism capable of protracting the penetrating cartridge towards the body of the patient, where protraction of the penetrating cartridge results in insertion of the subcutaneously insertable element into the body of the patient.

US 2009/0198191 discloses patches for medical devices, wherein in various embodiments, an adhesive patch of a medical device may have selective areas with adhesive material of varying adhesion strengths. In other embodiments, an adhesive patch of a medical device may include adhesive material that may be activated by a catalyst to increase or decrease the adhesion strength of the adhesive material. In further embodiments, a medical device may include a pierceable membrane containing an agent, the pierceable membrane being positioned to be pierced by a needle and to cause some of the agent to be carried to the user-patient.

U.S. Pat. No. 7,455,663 B2 discloses an infusion medium delivery system, a device and method for delivering an infusion medium to a patient-user, including a needle inserter device, and a method for inserting a needle and/or cannula into a patient-user to convey the infusion medium to the patient-user.

WO 2009/004026 A1 discloses an inserter for an infusion set for intermittent or continuous administration of a therapeutic substance, such as for example insulin. The inserter comprises means for insertion and retraction of an introducer needle. With the inserter of this document, it is possible to introduce an insertion needle when placing a medical device subcutaneously or transcutaneously.

SUMMARY

According to one embodiment, a cannula assembly may include a cannula module and an inserter module. The cannula module may include a skin-contacting surface for placing on an outer surface and a cannula having a pre-operational state and an operational state. In the pre-operational state the cannula is retracted with respect to the skin-contacting surface. In operational state the cannula projects beyond the skin-contacting surface. The inserter module is coupled to the cannula module in the pre-operational state. The inserter module may include an energy store and an activation mechanism. The energy store includes stored potential energy. When the energy store is at least partially discharged, the stored potential energy is transformed to kinetic energy that moves the cannula from the pre-operational state to the operational state. The activation mechanism is triggerable from outside the cannula assembly with a trigger device. The activation mechanism prevents the energy store from being discharged before it is triggered by the trigger device, and enables the energy store to be discharge after it is triggered by the trigger device to force the cannula from the pre-operational state into the operational state.

In another embodiment, a cannula system for administering a fluid is provided. The cannula system may include a disposable cannula assembly including an energy store and a cannula. The cannula moves from a pre-operational state to an operational state using energy supplied by the energy store. A movement is triggered from outside the disposable cannula assembly. A reusable trigger device is connected to and removable from a cannula assembly. The reusable trigger device triggers the movement of the cannula.

In a further embodiment, a method for delivering fluid to a cannula is provided. The method may include: receiving a trigger device with a cannula assembly comprising a cannula module and an inserter module, wherein the inserter module includes an energy store and an activation mechanism; receiving an input with the trigger device; transforming the input into a trigger of the activation mechanism of the inserter module, wherein the energy store becomes dischargeable; discharging at least in part the energy store; and moving the cannula from a pre-operational state into an operational state using energy of the energy store.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
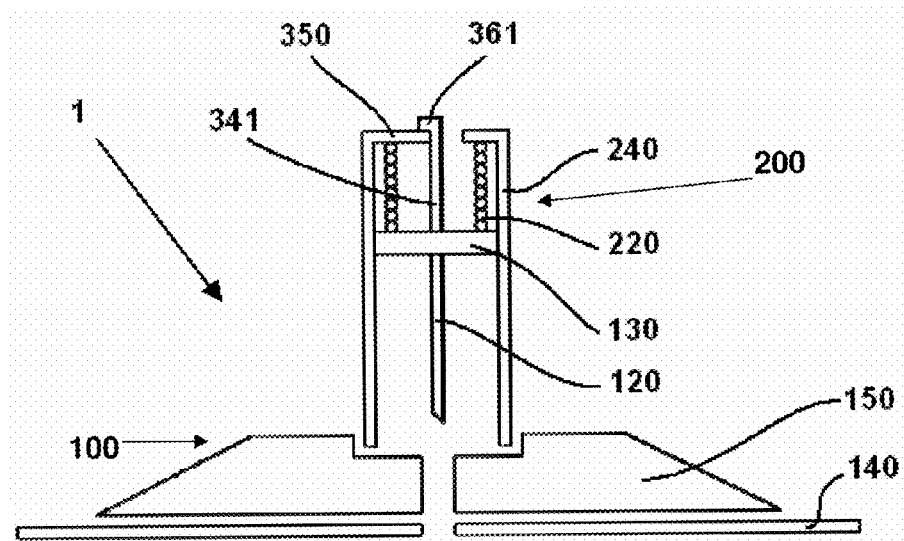
FIG. 1 schematically depicts a cannula assembly according to one or more embodiments shown and described herein.

User-friendly cannula assemblies for reducing inadvertent activation are described herein.

In accordance with one embodiment, a cannula assembly for transcutaneous fluid or liquid transport may be used with a trigger device for triggering an activation mechanism of the cannula assembly. The cannula assembly comprises a cannula module and an inserter module which may be disposable.

The cannula module may include a skin-contacting surface such as, for example, an adhesive layer, or an attachment to be placed or stably fixed to an outer surface of an object or the skin of a body (e.g., the skin of a user). The cannula module also may include a cannula having a hollow structural element adapted to protrude forward through the skin of the user and remain in the tissue for the duration of use. A fluid or drug can be administered through the structural element. The structural element can be a hollow steel cannula with a pointed tip or a soft, flexible tube (e.g., made of Teflon), which may be inserted by a guiding needle. The cannula comprises a fluid inlet at a distal end relative to the skin-contacting surface, and a fluid outlet at a proximal end relative to the skin-contacting surface. The cannula is adapted to be inserted through the outer surface of the object or the skin of the user, wherein the fluid inlet is in fluid communication with the proximal end portion and with the fluid outlet.

The cannula may be configured to assume two states: a pre-operational or initial state and an operational or final state. In the pre-operational state, the cannula is retracted relative to the skin-contacting surface such that it does not project from the skin-contacting surface. In the operational state, the cannula is advanced relative to the skin-contacting surface and projects from the skin-contacting surface. In accordance with one embodiment, the needle is adapted to pierce the user's skin, thus enabling a fluid or liquid to be transported from the fluid inlet into the body of the user.

The disposable inserter module can be designed to be coupled to the cannula module in the pre-operational state of the cannula. In the operational or piercing state, the cannula can be adapted to penetrate the skin and/or tissue of the body, thus allowing a fluid or liquid to be transported into the body.

In accordance with one embodiment, the inserter module is designed to be releasably coupled to the cannula module and to be separated from the cannula module in the operational state of the cannula.

The inserter module may include an energy store having stored potential energy and the activation mechanism. The energy store is designed as an energized or energizable actuating means such as a biased spring member that transforms stored or potential energy into kinetic energy when discharged, a pyrotechnic material that undergoes an exothermic chemical reaction in order to produce kinetic energy when ignited, a gas which is adapted to expand when heated, an electromagnetic device which is adapted to move when triggered and/or when an electric current is passed through it, or a magnetic device which is adapted to move when triggered.

If the energy store acts as an energized actuating means, it can be prevented from being discharged by blocking means, and when the blocking means is released the energy store may be discharged and the cannula may be moved. If the energy store acts as an energizable actuating means, it can be adapted to be discharged by an activating means, wherein activating, firing or triggering the activating means can enable the energy store to be discharged.

The inserter module may be configured to move the cannula from the pre-operational state to the operational state using the energy of the energy store or by at least partially discharging the energy store. In accordance with one embodiment, the inserter module is designed to bear the cannula module and to position the cannula at a desired location on the surface of the object such as, for example, at a desired angle to the skin.

The activation mechanism may include the blocking or activating means in order to prevent the energy store from being discharged and maintain the pre-operational state of the cannula, or to enable the energy store to be discharged and force the cannula into the operational state. As used herein, the phrase "force the cannula" means to move, to shift, to advance, to push, or to press the cannula axially along a casing or body of the inserter module.

The activation mechanism can be triggered from outside the cannula assembly by the trigger device. Triggering can, for example, involve transferring a force, movement, or mechanical impulse from the trigger device to the activation mechanism in order to release the blocking means or initiate the activating means in order to advance the cannula. In accordance with one embodiment, the activation mechanism is designed such that it can only be triggered by a trigger device which matches the activation mechanism (e.g., fulfilling a dedicated match criterion).

Triggering is possible from outside the cannula assembly. In accordance with one embodiment, triggering is only possible from outside the cannula assembly. The trigger device can be assembled together with a medical device or diabetes therapy device such as a glucose meter or a fluid supply or an infusion pump, wherein the trigger device and the medical or diabetes therapy device forms a single physical entity. A reusable triggering medical or diabetes therapy device can be cost-efficient to the user. For example, the complexity of the cannula assembly (e.g., the disposable modules) can be reduced by relocating the trigger device outside the cannula assembly.

The energy store can be a coil spring or a gas spring, for example a compression or extension spring supported on one side by being axially fixed to the body and on the other side by being axially fixed to a plunger.

The energy store can also be a pyrotechnic device which is adapted to ignite a pyrotechnic material or to expand a gas when exogenously triggered, for example by an ignition device in order to axially advance the plunger and/or the cannula.

In one embodiment, the activation mechanism comprises a trigger interface which is adapted to receive an exogenous or external trigger signal or trigger effect and to convert the trigger signal or trigger effect into a mechanical activating effect, magnetic activating effect, electric activating effect, electromagnetic activating effect, hydraulic activating effect, thermal activating effect, pneumatic activating effect, pyrotechnic activating effect, or combinations thereof. A trigger effect can be a trigger signal, such as a force, a voltage, an electric field, or a magnetic field. The activating effect can be a force or momentum which is exerted on a blocking means or blocking element. The blocking element can be designed to prevent the energy store from being discharged, until the blocking element is released from a blocking position in order to discharge the energy store and move the cannula.

A mechanical activating effect can be a force which is exerted, for example by a moving or shifting actuator on a pivoting retaining hook. Pivoting the retaining hook can release the retaining hook from an engagement with a retaining element, thus enabling the energy store such as, for example, a biased coil spring or gas spring coupled to the retaining hook, to be discharged.

A magnetic activating effect can be a magnetic force which is exerted by a permanent magnet or an electromagnet on a blocking element such as, for example, a pivoting retaining hook comprising a top which includes a permanent magnet or an electromagnet.

A pneumatic activating effect can be a pneumatic force exerted, for example, by releasing a gas spring integrated in the trigger device and fluidly connected to the activating mechanism, which exerts a force or momentum on the activating mechanism.

A thermal activating effect can be achieved by heating a gas contained in the cannula assembly, in order to generate a mechanical force or momentum.

A hydraulic activating effect can be achieved by a fluid or liquid such as, for example, insulin which is supplied from outside the cannula assembly. In accordance with one embodiment, the liquid can be supplied from the trigger device, a medical device, or a diabetes therapy device which is coupled to or integrated with the trigger device. For example a liquid can be supplied in order to wet a spongy element of the activating mechanism. The liquid changes the consistency of the spongy element and consequently moves a blocking element supported by the spongy element.

An electric activating effect can be an electric field which acts on an activating element, such as an ignition device, in order to enable the energy store, such as a pyrotechnic device, to be discharged. The activating means can be designed to enable the energy store to be discharged when triggered, activated, fired, or released.

In one embodiment, the activation mechanism comprises a security mechanism designed to help prevent the energy store from being accidentally discharged without having been triggered. An accidental discharge could be caused by inadvertent mechanical shocks acting on the cannula assembly initiated by a user before triggering.

The security mechanism can be adapted to switch from a blocking state in which the security mechanism prevents the energy store from being discharged (e.g., when the trigger device is detached from the cannula assembly), to a releasing state in which the energy store can be discharged. The security mechanism can be adapted to interact with key elements of the trigger device, wherein it is only possible to switch from the blocking state to the releasing state if the key elements of the trigger device and the security mechanism of the activation mechanism fulfill corresponding criteria.

A matching criterion can be that a shape of the key elements of the trigger device fit or match correspondingly shaped elements of the security mechanism in order to allow the security mechanism to enter the releasing state. The security mechanism can comprise a retaining pin which is levered on a fulcrum from the blocking state, in which the retaining pin prevents the retaining hook from pivoting, to the releasing state, in which the retaining pin is released in order to be pivoted. In accordance with one embodiment, an opening in the trigger device, a medical, or diabetes therapy device comprising the trigger device is designed to receive a bar-shaped inserter module. A wall enclosing the opening can comprise a key element such as a release buckle, which is adapted to release a levered retaining pin of the security mechanism. The security mechanism is adapted to engage with the release buckle when the inserter module is inserted into the opening of the trigger device, medical, or diabetes therapy device.

In some embodiments, a reed switch configured to be closed by a magnet in the triggering device is provided in the cannula assembly. For example, a reed switch may be provided in cannula assembly that cooperates with an electric trigger and a pyrotechnic device. Alternatively, it is possible to provide an RF transmitter in the triggering device and a corresponding receiver in the cannula assembly. In this case, the matching criterion can be a code which is transmitted from the triggering device. In another embodiment, triggering is only possible when the inserter module is inserted into the opening of the trigger device. The release buckle of the trigger device levers the retaining pin of the inserter module when the inserter module is advanced into the opening of the trigger device, medical, or diabetes therapy device.

If triggering is dependent on an external trigger device and an activation mechanism fulfilling certain matching criteria, the operating security of the cannula assembly can be improved by reducing the risk of the cannula assembly being inadvertently or accidentally activated.

In one embodiment, the activation mechanism comprises or operates as a blocking mechanism which prevents the energy store from being discharged such as, for example, when utilizing a mechanical, magnetic, electromagnetic, hydraulic, thermal, or pneumatic activating effect. The blocking mechanism can be triggered from outside the cannula assembly to be released, thus enabling the energy store to be discharged or resulting in the energy store being discharged.

In one embodiment, the activation mechanism is adapted to be triggered by moving a blocking element. In accordance with another embodiment, the blocking element forms part of the trigger interface. Thus, the blocking mechanism can simultaneously receive an activating effect and control the discharge of the energy store. The blocking element can be releasably attached to a retaining element in order to prevent the energy store from being discharged, and can be adapted to be detached from the retaining element by the activating effect in order to discharge the energy store.

Accordingly, security features can be incorporated in order to make handling the cannula assembly more secure such as, for example: the activation mechanism comprises a blocking element and a retaining element; the blocking element is releasably attached to the retaining element in order to prevent the energy store from being discharged; the blocking element is adapted to be detached from the retaining element by the activating effect; detaching the blocking element from the retaining element causes the energy store to be discharged; the activation mechanism can be triggered by moving the blocking element; and/or the blocking element optionally forms part of the trigger interface.

The inserter module can comprise an elongated cylindrical body. The cannula module can comprise a plunger mounted in it for a longitudinal shifting movement within the body of the inserter module between a retracted position and an advanced position. The energy store may engage with the plunger in order to advance the plunger when the energy store is discharged. The cannula can be axially fixed to the plunger such that advancing the plunger from the retracted position to the advanced position moves the cannula from the non-operational to the operational state.

The retaining elements of the activation mechanism can comprise a retaining hook and a retaining bearing or bearing element which are designed to assume a blocking state and a releasing state. When in the blocking state, the retaining hook is releasably engaged with the retaining bearing and the energy store is prevented from being discharged in the blocking state. When in the releasing state, the retaining hook is released from the retaining bearing and the energy store is allowed to be discharged.

The retaining hook can be a pivoting retaining hook comprising a hooked end releasably engaged with the retaining bearing, and an opposite, straight end, which pivots on and is axially fixed to the plunger. The pivoting retaining hook can be released from the retaining bearing by a lateral force which pushes against the hooked end of the retaining hook and moves the retaining hook from the blocking state to the releasing state.

The retaining hook can be an axially shiftable retaining hook comprising a hooked end releasably engaged with the plunger and an opposite end, which is connected to a bistable elastic element and axially fixed such that it can be separated. The bistable elastic element has two equilibrium states. The transition of the bistable elastic element from a blocking state to a releasing state enables the retaining hook to transition from the blocking state to the releasing state.

The bistable elastic element can be configured such that a transition from the blocking state to the releasing state is enabled by feeding a triggering fluid or liquid to the spongy element. For example, the bistable elastic element may be supported by a spongy element having a higher consistency in a dry state and a lower consistency in a moist state.

The retaining hook can be a laterally shiftable retaining hook comprising a first hooked end which is releasably engaged with the plunger, and a second hooked end which is connected to the bistable elastic element and laterally fixed such that it can be separated. The bistable elastic element may prevent the retaining hook from laterally shifting in the blocking state and enable the retaining hook to laterally shift in the releasing state.

The retaining hook can be a levered retaining hook comprising a hooked end which is releasably engaged with the plunger, and an opposite end which can be moved by an exogenously applied lateral force. The lateral force may lever the hook on a fulcrum and switch from the blocking state to the releasing state.

The embodiments described herein relate to a trigger device for triggering an activation mechanism of a cannula assembly. The trigger device may comprise an actuator which is adapted to trigger, i.e., move, the activation mechanism of the cannula assembly and a control element. In accordance with one embodiment, the control element is gripped by a user and manually operated by the user in order to initiate a triggering process for the actuator.

In accordance with one embodiment, the control element is adapted to be manually gripped by the user or to receive an operating effect from, for example, a medical or diabetes therapy device which is coupled to or integrated into or with the trigger device. The actuator may be coupled to the control element in order to exert an activating effect when the control element is operated.

In one embodiment, the trigger device is adapted to convert a user operation (i.e., a received input) such as, for example, touching, pushing, pulling or rotating the control element, into an externally supplied activating effect exerted on a blocking element of the activation mechanism. The activating effect triggers, i.e., moves, the blocking element and may be a mechanical activating effect, electromagnetic activating effect, thermal activating effect, hydraulic activating effect, pneumatic activating effect, or combinations thereof.

The actuator may comprise a release element adapted to be advanced outside the trigger device to interact with a retaining element of the activation mechanism. The interaction transfers or exerts a mechanical effect such as a shifting force on the retaining element.

The release element can comprise any of the following: a shiftable trigger pin or shiftable release plug adapted to exert an outward linear force; a shiftable wedge-shaped element adapted to exert an outward lateral force; a magnet which can be moved and/or activated and is adapted to exert an outward, variable magnetic force; and/or an electrical circuit, if for example a pyrotechnic device is used.

The trigger device can comprise a trigger body or housing for a control element and an actuator. The trigger body and control element can be designed to be substantially identical. For example, the trigger body may be a parallelepiped, a cuboid, or a cylindrical body comprising an opening for accommodating the inserter module. The actuator can be embodied by one or more bar-shaped elements which protrude onto, into or contact the inserter module for exerting an activation effect, such as a pushing effect on a blocking element of the activation mechanism.

Alternatively, the trigger body, control element and actuator can be designed to be substantially identical. For example, a fluid connector of a fluid source or infusion pump may be connected or attached to the inserter module. The fluid connector can be adapted such that attaching or connecting the fluid connector to the inserter module exerts an activation effect in order to trigger the activation mechanism of the cannula assembly. The activation effect may be, for example, a pushing effect on a blocking element of the activation mechanism, The trigger device may comprise a trigger interface which is adapted to transfer the activation effect or triggering information to the activation mechanism. In accordance with one embodiment, the trigger interface is a mechanical interface comprising the actuator for transferring the activation effect, or an electrical or radio interface for transferring the triggering information.

The actuator and/or the control element can be included or integrated in a medical or diabetes therapy device such as, for example, a glucose meter, or a fluid pump (e.g., an infusion pump or an insulin pump). Optionally, the actuator and/or the control element can comprise the medical or diabetes therapy device.

The trigger device can comprise key elements for interacting with a security mechanism of the cannula assembly which is adapted to be switched from a blocking state to a releasing state. When in the blocking state, the security mechanism prevents an energy store from being discharged. When in the releasing state, the energy store can be discharged. In certain embodiments, the key elements or the security mechanism can only interact if the key elements or the security mechanism fulfill matching criteria.

In accordance with one embodiment, the security mechanism and the blocking mechanism of the cannula assembly are adapted to be cascaded or to operate in succession. The security mechanism can block the blocking mechanism against being released for as long as the matching criteria between the key elements and the security mechanism are not fulfilled.

The embodiments described herein relate to a medical or diabetes therapy device such as a glucose meter, an infusion pump or fluid connector comprising a trigger device. The medical or diabetes therapy device can be shaped as a cylinder or a box with a cross-section adapted to match a corresponding means of the activation mechanism. In accordance with one embodiment, the activation mechanism can only be triggered by a trigger device which matches the activation mechanism, thus fulfilling matching criteria. For example the physical form of the medical or diabetes therapy device may be adapted to fit a correspondingly shaped inserter module.

The trigger device or the medical or diabetes therapy device can comprise a security mechanism designed to match a security mechanism of an activation mechanism of a cannula assembly.

Optionally, an opening in the medical or diabetes therapy device which has a specific cross-section or profile can be designed such that it can only receive a corresponding or complementary shape such as, for example, a bar-shaped inserter module having a suitably shaped cross-sectional profile. In one embodiment, triggering is only possible when the inserter module is inserted into the opening of the medical or diabetes therapy device.

If matching criteria have to be fulfilled prior to triggering, the operating security of the cannula assembly may be improved by reducing the risk of the cannula assembly being inadvertently or accidentally activated.

The embodiments described herein relate to a cannula system comprising a cannula assembly and a trigger device.

In one embodiment, a cannula system which is to be used with a fluid source, liquid supply or a pump for delivering a fluid or liquid to the cannula, such as an infusion pump. The cannula system comprises a disposable cannula assembly and/or a reusable trigger device.

In one embodiment, the cannula assembly comprises an energy store and a cannula, wherein the cannula can be moved from a pre-operational state to an operational state using the energy of the energy store and the movement is triggered from outside the cannula assembly. The trigger device can be connected, such that it can be separated, to the cannula assembly or energy store in order to trigger the movement of the cannula.

In one embodiment, the trigger device is distinct from the cannula assembly and/or from the energy store.

A trigger device may comprise trigger interface of the having an actuator. The trigger device can be designed to interact with a trigger interface of the cannula assembly in order to transfer and/or convert a trigger into an activating effect. The activating effect may trigger an activation mechanism of the trigger device and may be a mechanical activating effect, an electromagnetic activating effect, a thermal activating effect, a hydraulic activating effect, a pneumatic activating effect or a combination thereof.

A release element of the trigger device designed to interact with a retaining element of the activation mechanism may comprise one of the following elements: a shiftable trigger pin; a shiftable wedge-shaped element; a magnet which can be moved and/or activated; and a movable release plug.

The shiftable trigger pin can be adapted to laterally push a box-shaped cap which is fixed to a retaining hook, and pivot the retaining hook in order to release it from the engagement with a bearing element.

The shiftable wedge-shaped element can be adapted to engage with a wedge-shaped cap which is fixed to a retaining hook. In one embodiment, the wedge-shaped element is adapted to be complementary to the wedge-shaped cap, and pivot the retaining hook in order to release it from the engagement with a bearing element.

A magnet can be adapted to engage with a ferromagnetic cap which is fixed to a retaining hook. The magnet can be moved and/or activated to pivot the retaining hook and release it from the engagement with a bearing element.

The movable release plug can be fixed to a fluid connector and adapted to engage with a levered retaining hook in order to switch from the blocking state to the releasing state.

Embodiments of the present disclosure relate to methods for delivering a fluid or liquid to a cannula. In one embodiment, the method is applied to a cannula assembly comprising a cannula module, an inserter module and a trigger device which can be connected, such that it can be separated, to the cannula assembly. The inserter module comprises an energy store and an activation mechanism.

In one embodiment the method comprises: triggering the activation mechanism of the inserter module; moving the cannula from a pre-operational state to an operational state; and separating the trigger device from the cannula assembly. The activation mechanism is triggered by the trigger device, and enables the energy store to be discharged. The cannula is moved to an operational state using the energy of the energy store, for example, by at least partially discharging the energy store.

In accordance with one embodiment, the cannula system is suitably positioned on the surface or skin of an object or body before the triggering step is performed. Suitable positions for the cannula system include a desired inclination towards the surface of the object or body.

Methods according to the embodiments described herein can be performed without piercing the skin of a human or animal or can be performed in the absence of a human or animal body. Such methods can also be performed for the purpose of piercing the skin of a human or an animal.

In one embodiment, the energy store can be prevented from being discharged when the trigger device or a medical or diabetes therapy device comprising the trigger device is detached from the cannula assembly. Attaching the trigger device or the medical or diabetes therapy device comprising the trigger device to the cannula assembly enables the activation mechanism to be triggered, in order to discharge the energy store.

In accordance with one embodiment, the activation mechanism can only be triggered if matching criteria between key elements of the trigger device and a security mechanism of the cannula assembly are fulfilled.

In one embodiment, performing a triggering process of the trigger device can trigger the activation mechanism such as by exerting a force. The triggering process of the trigger device can also enable the activation mechanism to be triggered such as, for example, by attaching the medical or diabetes therapy device to the cannula assembly or by transferring triggering information from the trigger device to the cannula assembly via an electrical or radio interface.

In accordance with one embodiment, the activation mechanism can be triggered by enabling the security mechanism of the cannula assembly to switch from a blocking state to a releasing state. For example, the matching criteria between the key elements of the trigger device and the security mechanism of the cannula assembly have to be fulfilled in order to permit the energy store to be discharged.

In one embodiment, a triggering process of the trigger device induces an activating effect of the trigger device which is adapted to initialize the discharge of the energy store or to release at least one retaining element of the activation mechanism such as a security mechanism, in order to enable the energy store to be discharged.

In accordance with the embodiments described herein, the discharge can be enabled by switching the security mechanism from a blocking state to a releasing state. In one embodiment, it is only possible to discharge the energy store or to initialize the discharge in the releasing state of the security mechanism.

In one embodiment, triggering the activation mechanism involves at least one of the following: attaching the trigger device, such that it can be separated, to the cannula assembly; attaching a fluid connector or a medical or diabetes therapy device comprising the trigger device, such that it can be separated, to the cannula assembly; operating a control element of the trigger device; or channeling a fluid or liquid into the cannula assembly.

In one embodiment, discharging the energy store is enabled by at least one of the following: shifting an actuator of the trigger device; activating a motor in order to shift an actuator of the trigger device; activating a magnetic field in order to shift a plunger of the trigger device; wetting a spongy element of the activation mechanism in order to move at least one retaining element by lowering the consistency of the spongy element; or igniting a pyrotechnic device.

In one embodiment a method for delivering a fluid or liquid to a cannula utilizes: a cannula assembly comprising a cannula module and an inserter module, wherein the inserter module comprises an energy store and an activation mechanism; and a trigger device which can be connected, such that it can be separated, to the cannula assembly. The method includes: triggering the activation mechanism of the inserter module using the trigger device, thus enabling the energy store to be discharged; moving the cannula into an operational state using the energy of the energy store; and separating the trigger device from the cannula assembly.

In one embodiment, the energy store is prevented from being discharged when the trigger device is detached from the cannula assembly, and attaching the trigger device to the cannula assembly enables the activation mechanism to be triggered, in order to discharge the energy store.

In one embodiment, performing a triggering process of the trigger device triggers the activation mechanism or enables the activation mechanism to be triggered.

In one embodiment, a triggering process of the trigger device initializes the discharge of the energy store or releases at least one blocking element of the activation mechanism in order to enable the energy store to be discharged.

In one embodiment, triggering the activation mechanism includes at least one of the following: attaching the trigger device to the cannula assembly or energy store; attaching a fluid connector or a medical device or diabetes therapy device comprising the trigger device to the cannula assembly; operating a control element of the trigger device; and/or channeling a fluid or liquid into the cannula assembly. Discharging the energy store may be enabled or initiated by at least one of the following: shifting an actuator of the trigger device, manually or motor-driven, in order to exert a releasing force on a blocking element; wetting a spongy element of the activation mechanism in order to move at least one blocking element by lowering the consistency or structural strength of the spongy element; activating an ignition device in order to ignite a pyrotechnic device.

Figure 2:
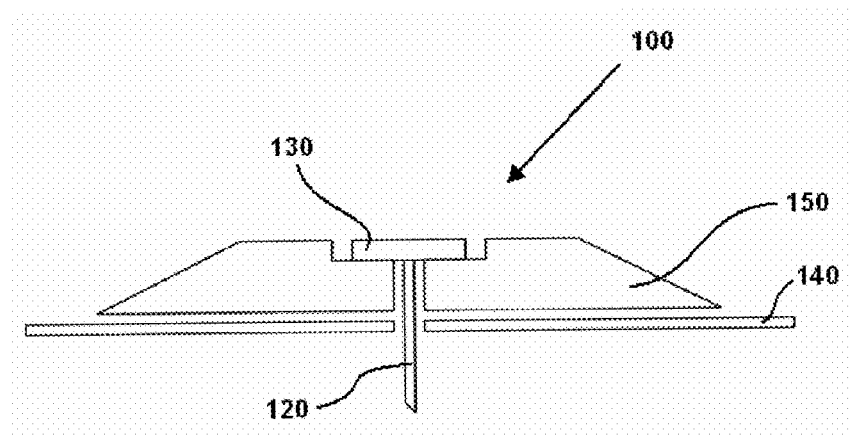
FIG. 2 schematically depicts a cannula module according to one or more embodiments shown and described herein.
Figure 3:
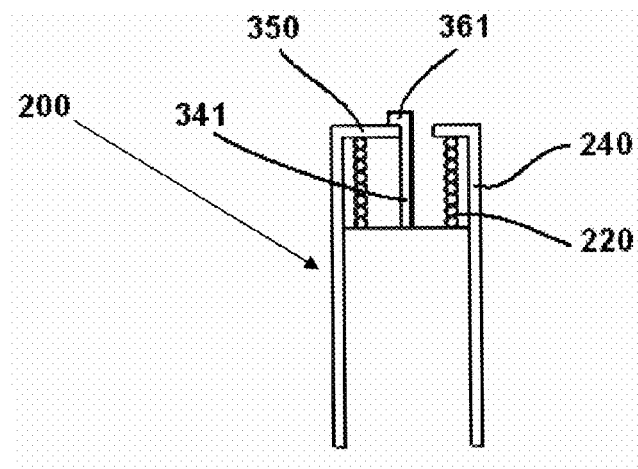
FIG. 3 schematically depicts an inserter module according to one or more embodiments shown and described herein.

Referring collectively to FIGS. 1 to 3, a cannula assembly 1 according to the embodiments described herein is schematically depicted. In one embodiment, the cannula assembly 1 comprises a cannula module 100 and an inserter module 200, which may be disposable.

As depicted in FIG. 2, the cannula module 100 comprises an adhesive layer disposed on the skin-contacting surface 140 which may be placed on a user's skin. The cannula module 100 also comprises a cannula 120 having a hollow structural element which remains in the tissue for the duration of use and through which a drug can be administered. The hollow structural element can be a hollow steel cannula with a pointed tip or a flexible cannula tube, which may be made of Teflon. In the latter case, a guidance needle is provided inside the cannula tube. The guidance needle has a pointed tip and is slightly longer than the flexible cannula tube, but is generally not hollow. The guiding needle pierces the skin and stabilizes the flexible cannula tube during insertion. Once insertion is complete, the guiding needle may be retracted and removed manually or by a spring.

The cannula 120 can be configured to assume two states: a pre-operational or initial state and an operational or final state. In the pre-operational state, depicted in FIG. 1, the cannula 120 is retracted relative to a skin-contacting surface 140, i.e., the pointed tip is above (higher on the page) the skin-contacting surface 140. In the operational state, depicted in FIG. 2, the cannula is advanced relative to the skin-contacting surface 140 and projects beyond the skin-contacting surface 140, i.e., the pointed tip is below (lower on the page) the skin-contacting surface 140.

Referring collectively to FIGS. 1 to 3, the inserter module 200 maybe releasably coupled to the cannula module 100 in the pre-operational state of the cannula 120, depicted in FIG. 1, and may be separated from the cannula module 100 in the operational state of the cannula 120, depicted in FIG. 2. The inserter module 200 comprises an energy store such as a biased spring 220, which is adapted to transform stored energy into kinetic energy when discharged, and an activation mechanism. In the depicted embodiment, the activation mechanism comprises a pivoting retaining hook 341, a bearing element 350, and a box-shaped cap 361.

The biased spring 220 can be prevented from being discharged by blocking means comprising a pivoting retaining hook 341 and a bearing element 350. The release of the blocking means can enable the biased spring 220 to be discharged and the cannula 120 to be moved. The activation mechanism can be triggered from outside the cannula assembly by a trigger device, as described herein. Triggering involves transferring a force from a trigger device to the activation mechanism in order to release the blocking means in order to advance the cannula 120.

In one embodiment, the blocking means comprise a pivoting retaining hook 341 and a bearing element 350. When in a blocking state, the pivoting retaining hook 341 is releasably engaged with the bearing element 350. When in a releasing state, the pivoting retaining hook 341 is released or disengaged from the bearing element 350. The biased spring 220 is prevented from being discharged in the blocking state, and allowed to be discharged in the releasing state. In another embodiment, the energy store may be a tensioned spring which is prevented from being relaxed in the blocking state, and allowed to be relaxed in the releasing state.

As depicted in FIGS. 1 and 3, the pivoting retaining hook 341 comprises a hooked end having a box-shaped cap 361 releasably engaged with the bearing element 350, and an opposite, straight end which pivots on and is axially fixed to a plunger 130. The pivoting retaining hook 341 can be released from the bearing element 350 by a lateral force which pushes against the box-shaped cap 361 on the hooked end of the pivoting retaining hook 341 and moves the pivoting retaining hook 341 from the blocking state to the releasing state.

Referring now to FIGS. 4 to 12, embodiments of a cannula system may comprise a trigger device integrated in a medical therapy device 450 such as a diabetes therapy device. The medical therapy device 450 may trigger or initiate the movement of the cannula 120. Alternatively, the cannula assembly 1 can be controlled and/or operated with or without mechanical contact between the cannula assembly 1 and the trigger device. As used herein, the phrase "diabetes therapy device" means a device used by a person in diabetes therapy such as a glucose meter or an insulin pump.

Figure 4:
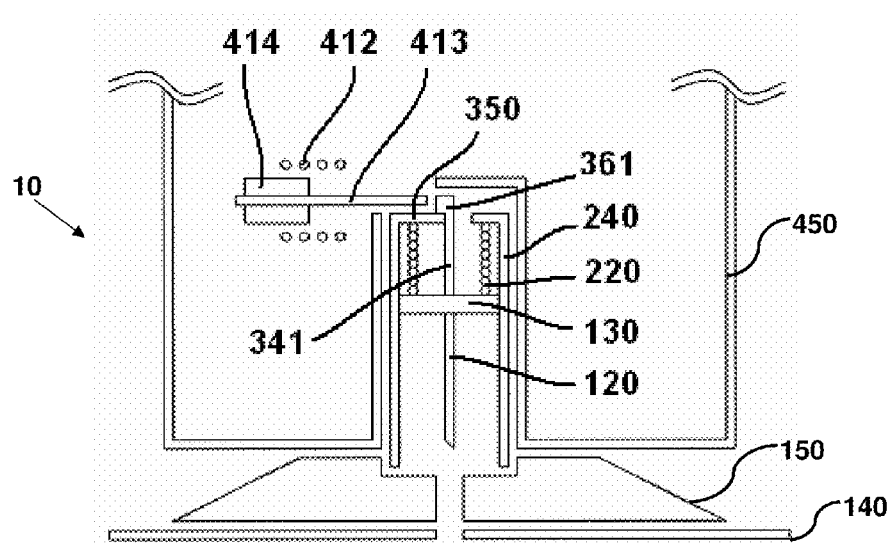
FIG. 4 schematically depicts a cannula system comprising a trigger device integrated in a medical or diabetes therapy device, wherein a mechanical activating effect is exerted by a shiftable pin which can be moved using an electromagnet according to one or more embodiments shown and described herein.

As depicted in FIG. 4, the trigger device comprises a shiftable pin 413 and an electromagnet 412 that cooperate via electromagnetism to trigger the insertion of the cannula 120. In one embodiment, the electromagnet 412 is energized by a current which causes the shiftable pin 413 to move laterally (to the right as depicted in FIG. 4). As the shiftable pin 413 is urged into the box-shaped cap 361 by the electromagnet 412, the shiftable pin 413 interacts with the box-shaped cap 361 on the pivoting retaining hook 341. The interaction causes the pivoting retaining hook 341 to deflect. When the box-shaped cap 361 is deflected beyond the bearing element 350, the biased spring 220 is released and acts on the plunger 130 attached to the cannula 120. Upon being released, the plunger 130 and the biased spring 220 move downwards. For example, if a patient's skin were beneath the cannula 120, the triggering would cause the cannula 120 to be inserted into the patient's skin. It is noted that, the shiftable pin 413 may be moved back into its initial position by another spring (not depicted) in the trigger device.

In the embodiment depicted in FIG. 4, the movement of the cannula 120 is limited when the plunger 130 contacts a cannula hub 150. The cannula 120 is fully inserted when the plunger 130 is in contact with the cannula hub 150. The cannula hub 150 is attached to the skin-contacting surface 140 and also comprises a fluid connector to the medical therapy device (not depicted in FIG. 4).

Additionally it is noted that once insertion is complete, the trigger device can be removed and followed by an inserter module 200.

Figure 5:
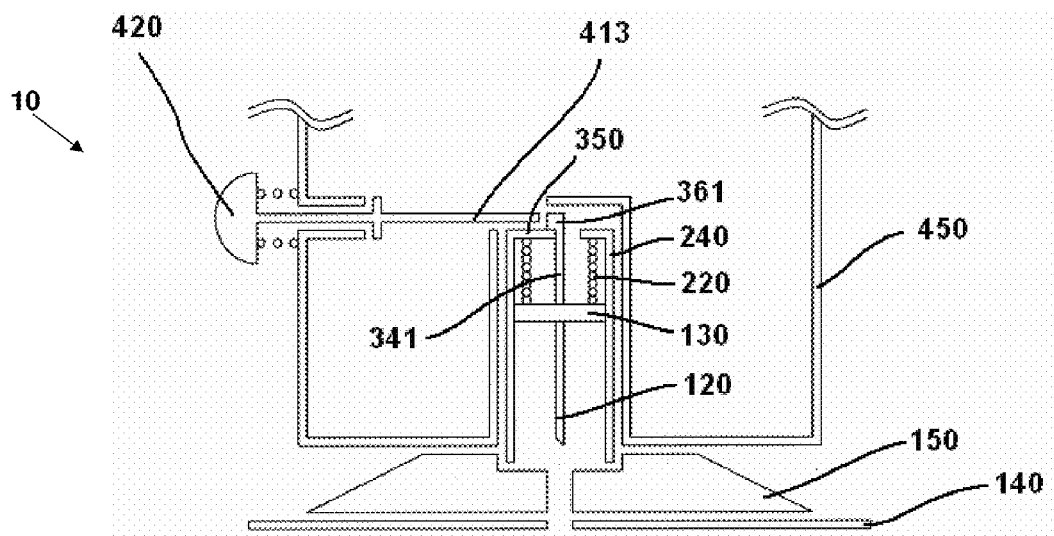
FIG. 5 schematically depicts a cannula system comprising a trigger device integrated in a medical or diabetes therapy device, wherein a mechanical activating effect is exerted by a shiftable pin which can be moved manually using a push button according to one or more embodiments shown and described herein.

Various modifications to the embodiments described herein are contemplated. For example, the shiftable pin 413, depicted in FIG. 4, could also be operated via a push button 420 included in the trigger device, as depicted in FIG. 5. For example, the push button 420 may receive a manually generated force and cause the box-shaped cap 361 to be deflected beyond the bearing element 350.

In the embodiments depicted in FIGS. 4 to 11, the medical therapy device 450 is attached to the cannula assembly 1 in order to initiate an insertion of the cannula. Insertion is triggered by a control element (e.g., the push button 420 depicted in FIG. 5).

Referring back to FIG. 4, a ferrite rod 414 or piston rod coupled to the shiftable pin 413 may be moved by an electromagnet 412. The movement of the ferrite rod 414 can move the pivoting retaining hook 341 until it is completely released and the cannula 120 is injected. In the embodiment depicted in FIG. 4, the energy store is a biased spring 220 which is held in a compressed state and released in order to insert the cannula 120. The pivoting retaining hook 341 interacts, prior to the insertion of the cannula 120, with a corresponding element (not depicted) of the inserter module 200 in order to hold the biased spring 220 in a compressed state and the cannula 120 in the pre-operational state.

Referring back to FIG. 5, movement of the push button 420 moves the pivoting retaining hook 341 until it is released. In further embodiments, it is also possible to use more than one push button 420 and more than one pivoting retaining hook 341, such as two of each. For example, the insertion of the cannula 120 maybe triggered only if both buttons are pushed.

Figure 6:
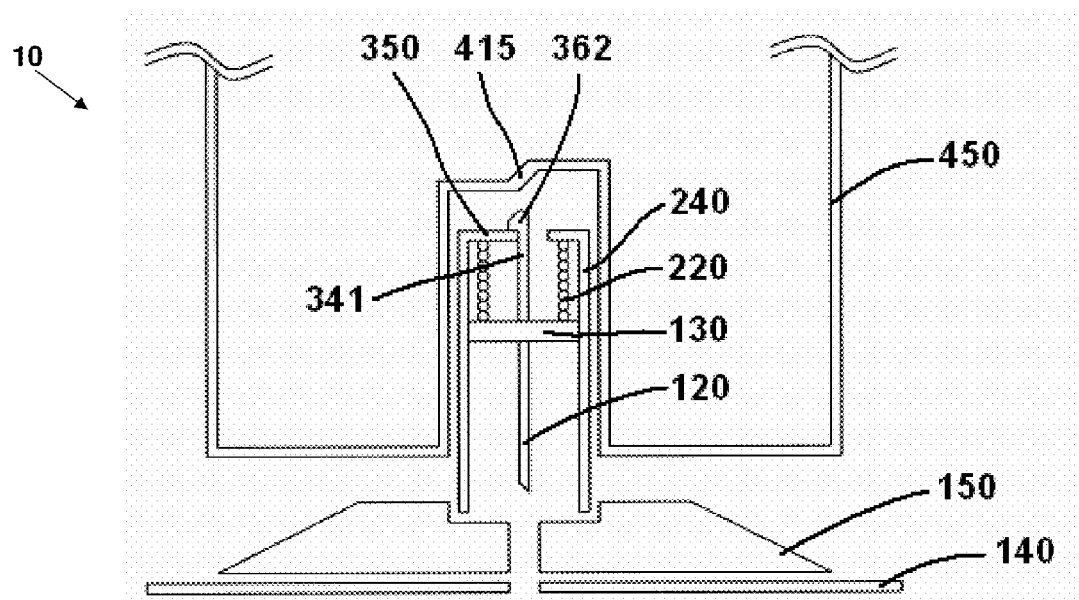
FIG. 6 schematically depicts a cannula system comprising a trigger device integrated in a medical or diabetes therapy device, wherein a mechanical activating effect is exerted by an element which can be moved vertically and is wedge-shaped on one side according to one or more embodiments shown and described herein.

In the embodiment depicted in FIG. 6, the pivoting retaining hook 341 is moved laterally by an inclined wedge-shaped surface on one side of a wedge-shaped element 415. For example, insertion of the cannula 120 may be triggered as the wedge-shaped element 415 moves downward until the pivoting retaining hook 341 is released.

Figure 7:
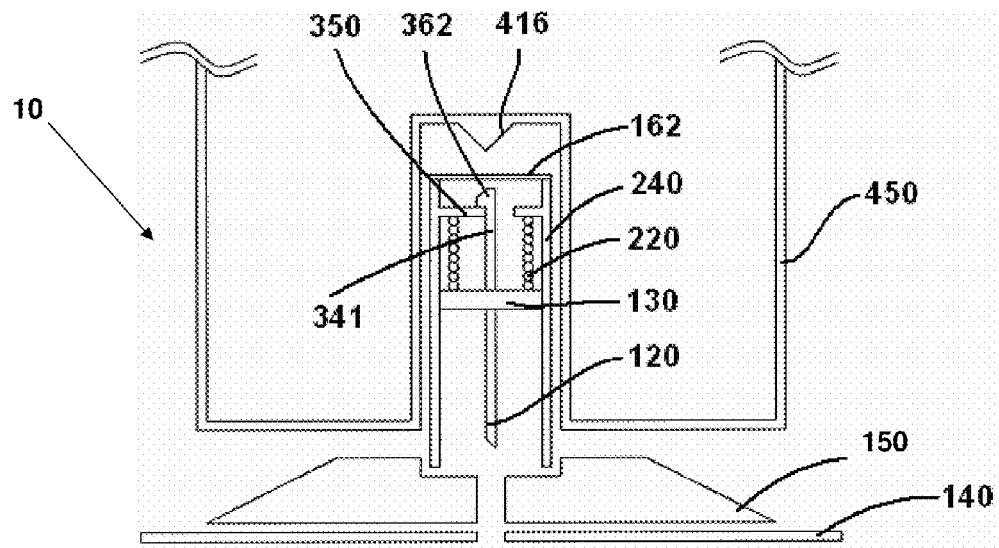
FIG. 7 schematically depicts a cannula system comprising a trigger device integrated in a medical or diabetes therapy device, wherein a mechanical activating effect is exerted by a wedge-shaped element which can be moved vertically according to one or more embodiments shown and described herein.

In the embodiment depicted in FIG. 7, triggering occurs when a prism-shaped or wedge-shaped element 416 is moved towards the pivoting retaining hook 341 until the pivoting retaining hook 341 is released and the cannula 120 is injected. In one embodiment, the wedge-shaped element 416 pierces an initially sterile barrier such as a septum 162 which covers the trigger device.

Figure 8:
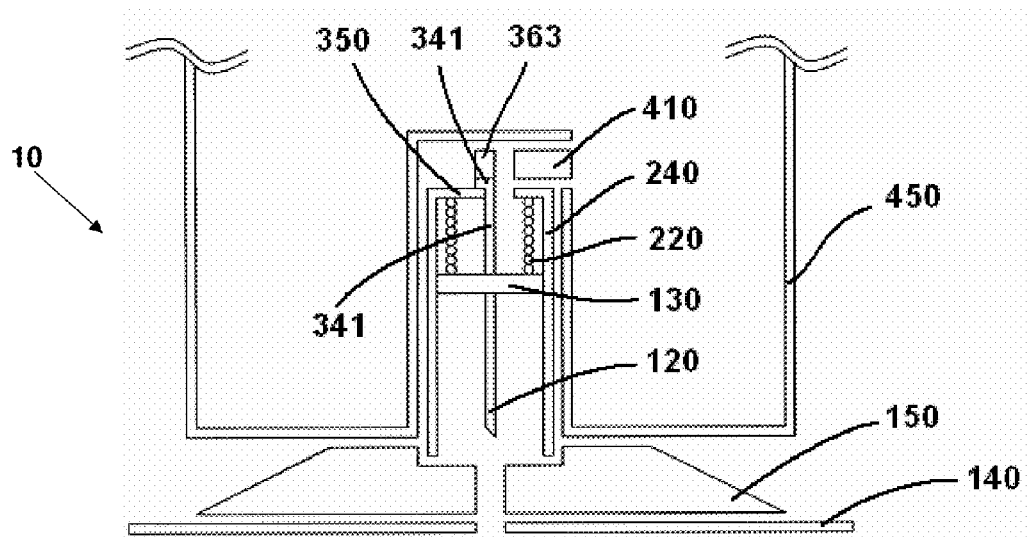
FIG. 8 schematically depicts a cannula system comprising a trigger device integrated in a medical or diabetes therapy device, wherein a magnetic activating effect is exerted by a magnet which can be moved according to one or more embodiments shown and described herein.

In one embodiment, depicted in FIG. 8, a cannula assembly 1 comprises a pivoting retaining hook 341 having a snapping element such as a metal element or a ferromagnetic cap 363. The ferromagnetic cap holds the biased spring 220 in its biased state. A permanent magnet 410 integrated into the medical therapy device 450 may be moved towards the pivoting retaining hook 341 until the pivoting retaining hook 341 is released and the cannula 120 is injected, i.e., triggering occurs.

Figure 9:
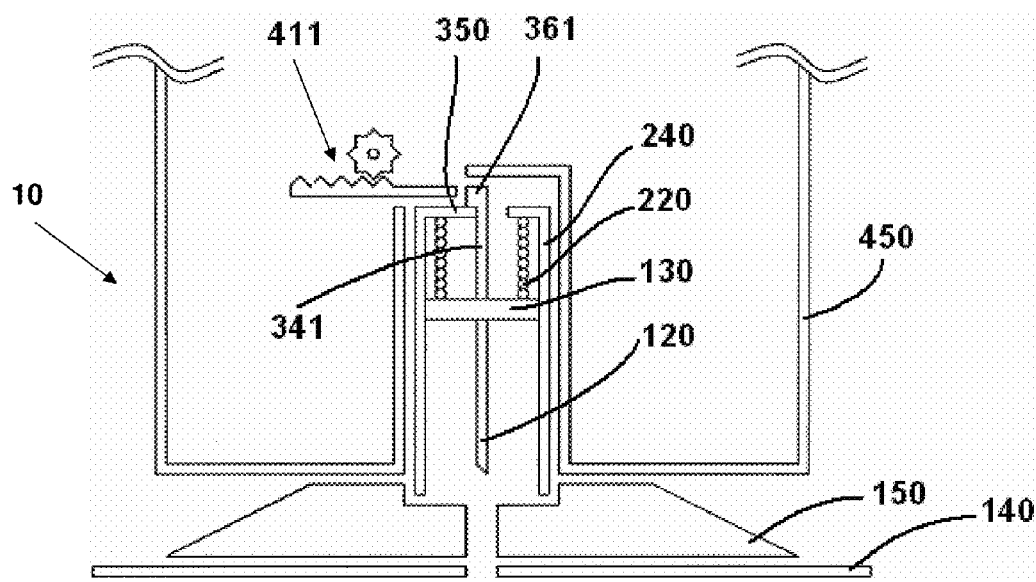
FIG. 9 schematically depicts a cannula system comprising a trigger device integrated in a medical or diabetes therapy device, wherein a mechanical activating effect is exerted by a motor-driven shiftable pin according to one or more embodiments shown and described herein.

In the embodiment depicted in FIG. 9, the trigger device is a motor-driven gear rack 411 that moves the activation mechanism, i.e., the pivoting retaining hook 341. The cannula 120 is injected when the pivoting retaining hook 341 is moved beyond the bearing element 350.

Figure 10:
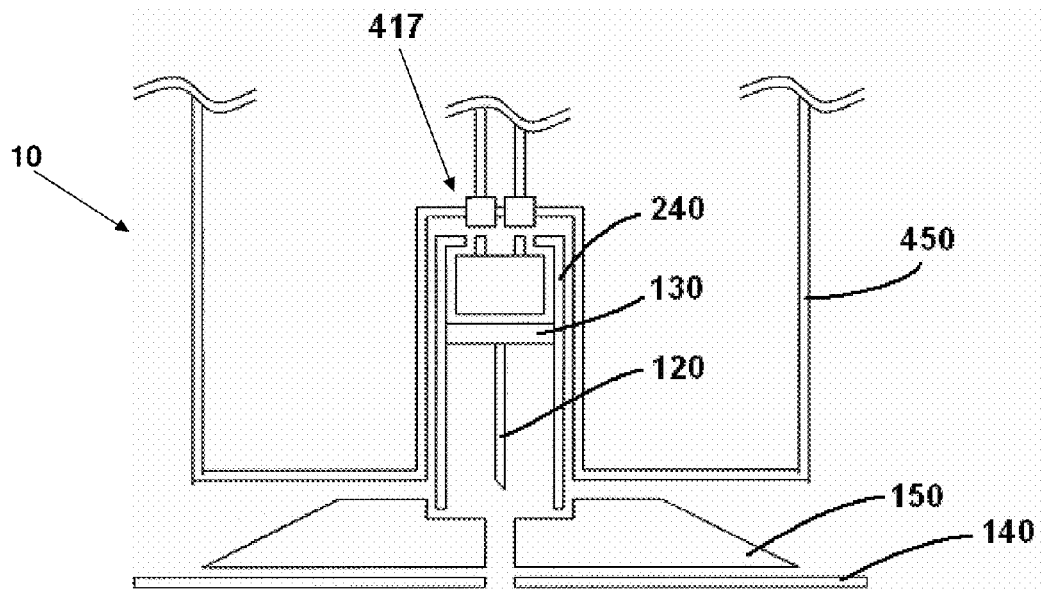
FIG. 10 schematically depicts a cannula system comprising a trigger device integrated in a medical or diabetes therapy device, wherein an electric field which activates an ignition device is applied in order to trigger a pyrotechnic device according to one or more embodiments shown and described herein.

Referring to FIG. 10, an embodiment of the cannula assembly 1 comprises an energy store. In the depicted embodiment, the energy store is a pyrotechnic device 417 which releases stored chemical energy in a controlled "explosion" upon receiving an electrical trigger signal via trigger contacts in the trigger device. The corresponding control and power circuitry for triggering the pyrotechnic device 417 may be included in the trigger device.

Figure 11:
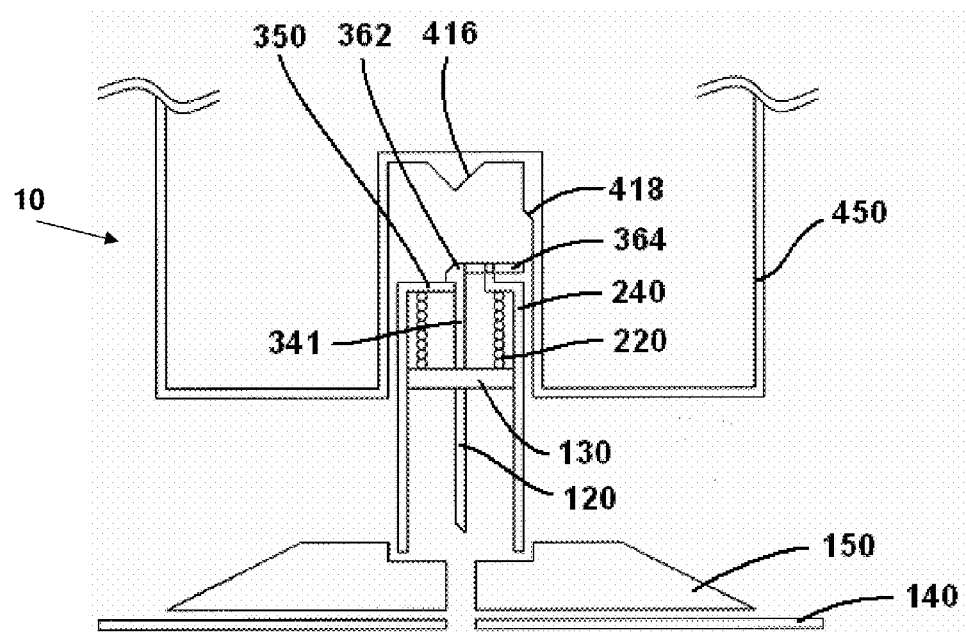
FIG. 11 schematically depicts a cannula system comprising a trigger device integrated in a medical or diabetes therapy device, wherein the trigger device comprises key elements which match a security mechanism of the cannula assembly and wherein a mechanical activating effect is exerted by a wedge-shaped element which can be moved vertically according to one or more embodiments shown and described herein.

Referring to FIG. 11, in one embodiment the trigger device is a wedge-shaped element 416 (e.g., prism-shaped) that is moved towards the activation mechanism, which is a pivoting retaining hook 341 in the depicted embodiment. For example, triggering occurs when the pivoting retaining hook 341 is released by the wedge-shaped element 416 and the cannula 120 is then injected.

The cannula assembly 1 depicted in FIG. 11 comprises a security mechanism 364 which is adapted to switch from a blocking state to a releasing state. When the security mechanism 364 is in the blocking state the energy store is prevented from being discharged. For example, when the trigger device is detached from the cannula assembly 1, a biased spring 220 can be prevented from discharging by a retaining pin. When the security mechanism 364 is in the releasing state the energy store can be discharged. Specifically, in the depicted embodiment, the security mechanism 364 is a retaining pin which can be levered on a fulcrum from the blocking state, in which the security mechanism 364 (e.g., retaining pin) prevents the pivoting retaining hook 341 from pivoting, to the releasing state in which the pivoting retaining hook 341 is released for pivoting.

In the embodiment depicted in FIG. 11, the top of the pivoting retaining hook 341 comprises a wedge-shaped cap 362 designed to facilitate an engagement between the retaining pin and the pivoting retaining hook 341 in the blocking state. The wedge-shaped cap 362 enables an engagement between a wedge-shaped element 416 and the pivoting retaining hook 341 to release the pivoting retaining hook 341 from its engagement with a bearing element 350. Once the pivoting retaining hook 341 is released the biased spring 220 can be discharged. The retaining pin can be levered on a fulcrum from the blocking state to the releasing state by a release buckle 418 of the trigger device. The release buckle 418 and the retaining pin are designed to match such that advancing the trigger device or the medical therapy device 450 comprising the trigger device from a distal position with respect to the skin-contacting surface 140 enables the retaining pin to be levered.

The security mechanism 364 is designed in a similar way to a locking device. For example, the medical therapy device 450 may comprise the release buckle 418 that operates as a key that can unlock the security mechanism 364. This "locking" ensures that the pivoting retaining hook 341 is not inadvertently released. Accordingly, the security mechanism 364 can be designed in a similar way to a mechanical lock. Thusly, the security mechanism 364 can prevent an insertion of the cannula 120 from being triggered inadvertently or through deliberate misuse. Triggering may be limited such that triggering is only possible using the corresponding counterpart or key such as, for example, a release buckle 418 in a medical therapy device 450.

Referring collectively to FIGS. 11A to 11F, an insertion sequence using the embodiment of the cannula system 10 shown in FIG. 11 is depicted.

Figure 11A:
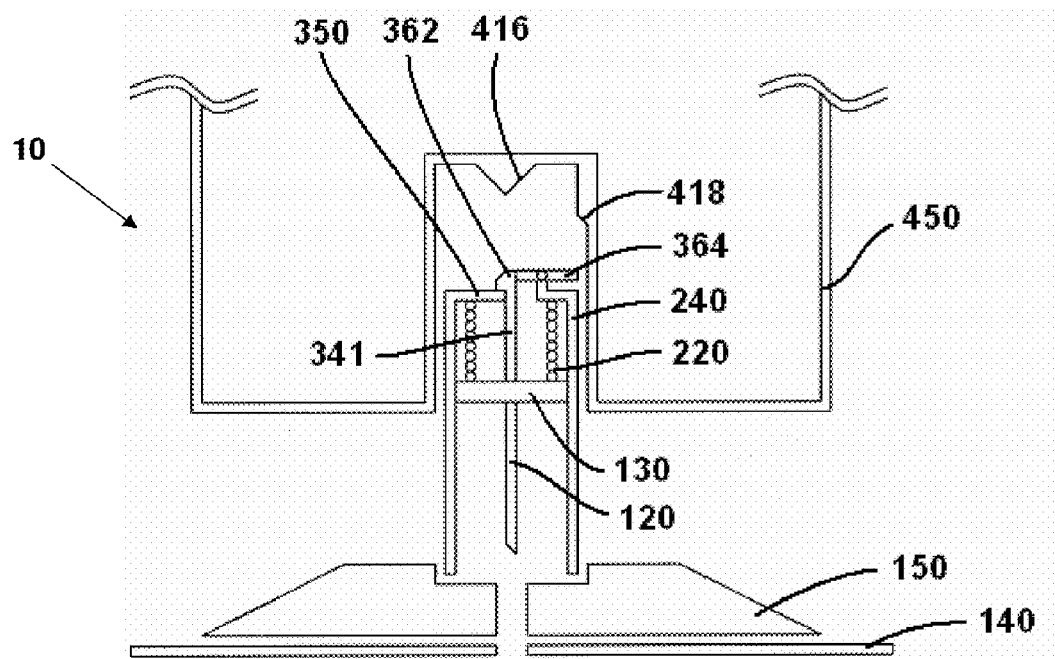
FIGS. 11A to 11F schematically depict an insertion sequence using the cannula system shown in FIG. 11 according to one or more embodiments shown and described herein.

In FIG. 11A, the inserter module 200 has been introduced into a corresponding opening of the medical therapy device 450. The pivoting retaining hook 341 is engaged with the bearing element 350, and the security mechanism 364 is engaged with the wedge-shaped cap 362 of the pivoting retaining hook 341.

Figure 11B:
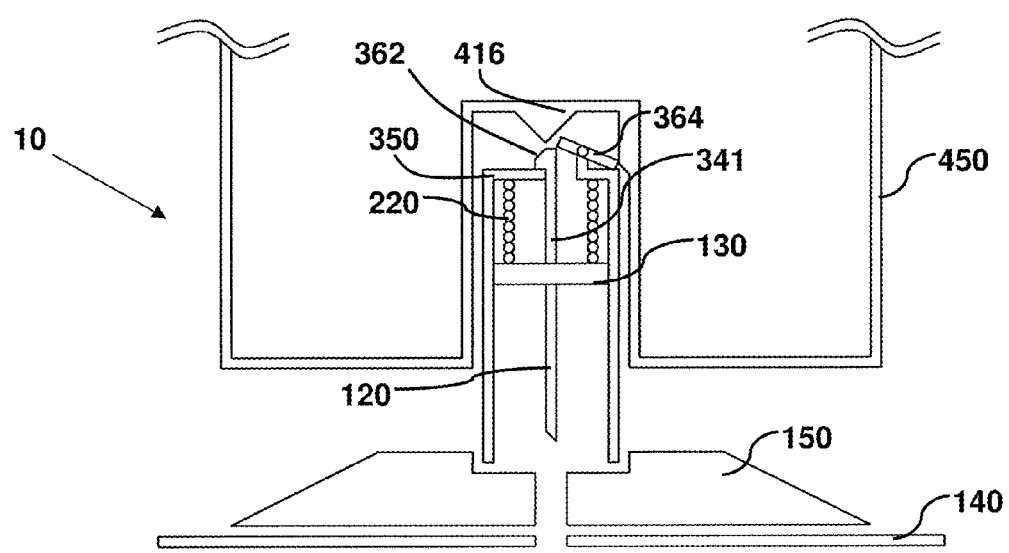

In FIG. 11B, the release buckle 418, which is part of the opening of the medical therapy device 450 (e.g., curved profile), tilts the security mechanism 364 (e.g., locking lever or levered retaining pin). The pivoting retaining hook 341 is no longer blocked or secured by the security mechanism 364.

Figure 11C:
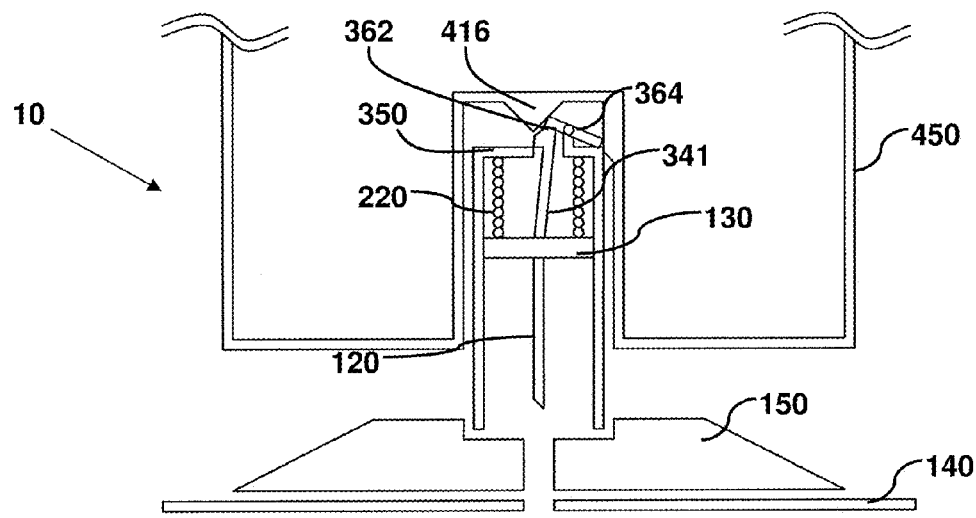

In FIG. 11C depicts the inserter module 200 being passed upwards and further into the corresponding opening. The pivoting retaining hook 341 is displaced by the wedge-shaped element 416 and released.

Figure 11D:
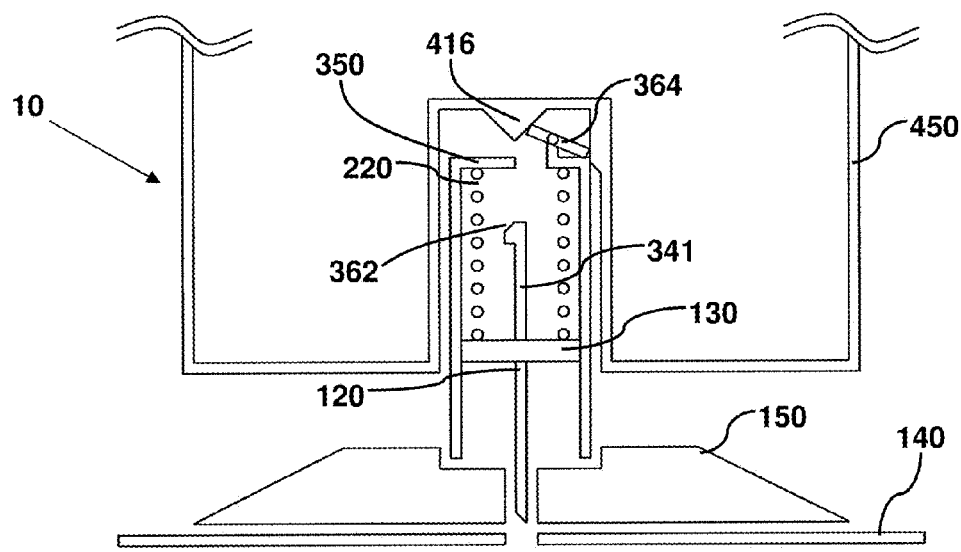

As depicted in FIG. 11D, releasing the pivoting retaining hook 341 frees the lock on the cannula 120 (e.g., needle assembly). The biased spring 220 can relax and move the cannula 120 towards the skin-contacting surface 140.

Figure 11E:
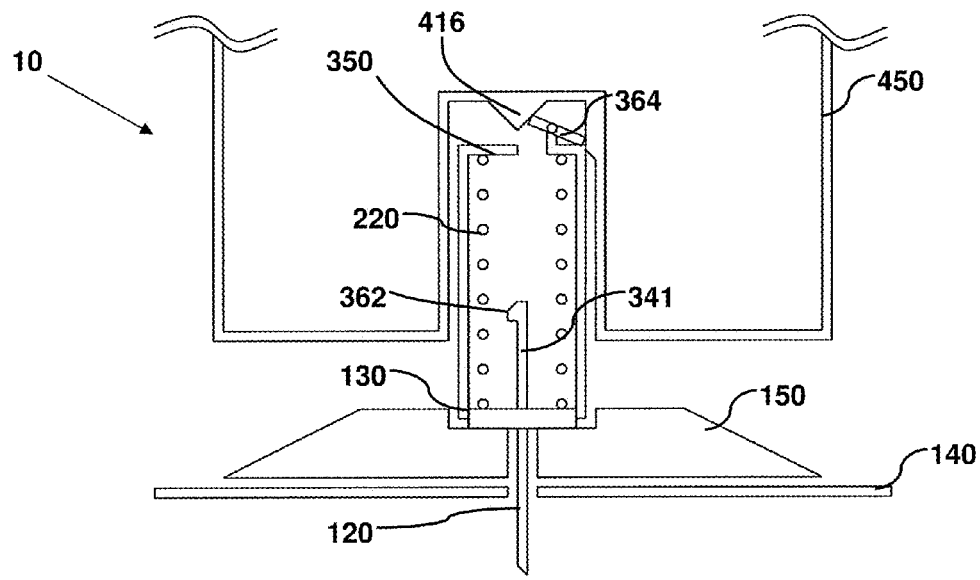

In FIG. 11E, the cannula 120 is advanced downward into contact with the cannula hub 150, i.e., its final position. In the final position, the cannula 120 snaps into the cannula hub 150. The inserter module 200 is also released from the cannula hub 150 (not depicted).

Figure 11F:
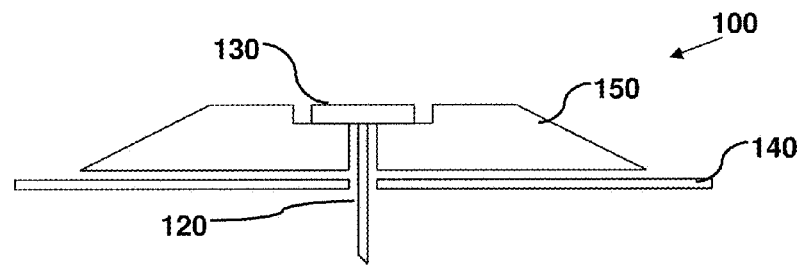

FIG. 11F depicts the cannula module 100 after the inserter module 200 has been removed. The cannula module 100 is ready to be attached to a fluid or liquid tube of a fluid source such as an infusion pump.

Figure 12A:
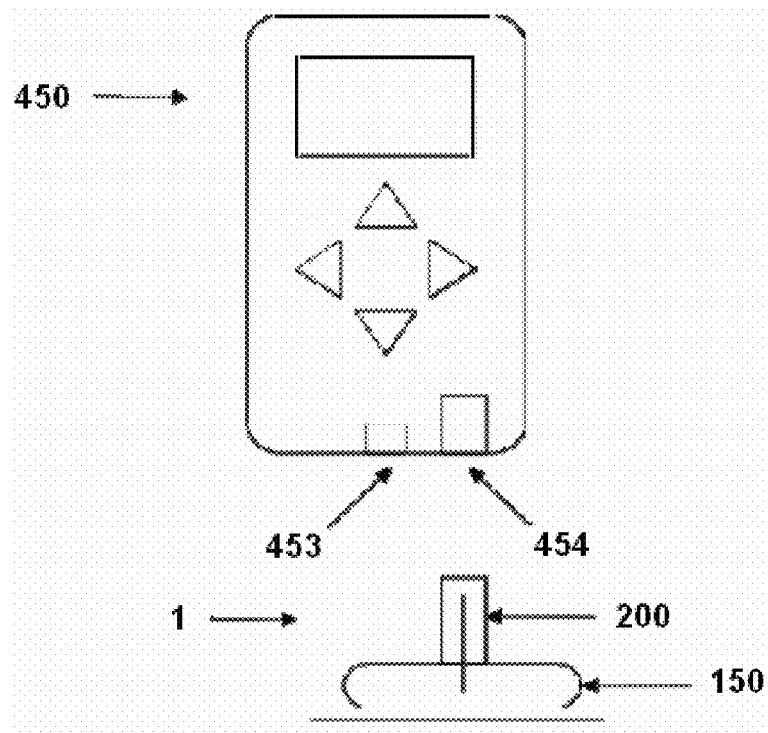
FIG. 12A schematically depicts a cannula system comprising a trigger device integrated in a medical or diabetes therapy device, wherein the triggering effect is exerted via a mechanical interface according to one or more embodiments shown and described herein.

FIG. 12A schematically depicts an embodiment of a cannula system 10 comprising a cannula assembly 1 and a medical therapy device 450 such as a glucose meter comprising an integrated trigger device. Alternatively, the trigger device can be integrated into an insulin pump or other diabetes therapy device. Inserting the cannula assembly 1 into a slot 453 of the medical therapy device 450 triggers the cannula assembly 1. The medical therapy device 450 may further comprise an electrical trigger interface 454. It is noted that in some embodiments the slot 453 and the electrical trigger interface may be integral.

Figure 12B:
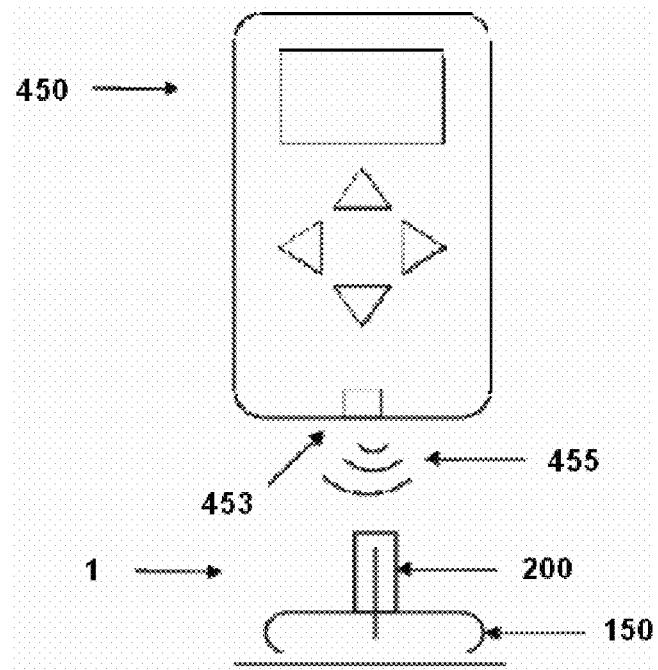
FIG. 12B schematically depicts a cannula system comprising a trigger device integrated in a medical or diabetes therapy device, wherein the triggering effect is exerted via a radio interface according to one or more embodiments shown and described herein.

FIG. 12B depicts a further embodiment of the cannula system 10, wherein the cannula assembly 1 is triggered via a radio trigger interface 455 of the medical therapy device 450.

Referring collectively to FIGS. 4 to 12, the mechanical components that are susceptible to abrasive wear may be integrated into the inserter module 200 rather than the medical therapy device 450. The inserter module 200 can be designed for a small number of applications or for only one application, thus permitting the inserter module 200 to be disposable. Furthermore, the probability that the inserter module 200 malfunctions due to abrasive wear can be reduced.

In the embodiments described herein, the medical therapy device 450 may comprise the trigger device, which can be small in volume for integration.

In some embodiments, the inserter module 200 may be made disposable without any controls.

Software functions can be integrated with the embodiments described herein. For example, a function whereby the insertion of the cannula 120 is triggered at a point in time that is determined using a random number generator within a several-second period or e.g. 10-second period, such that the patient is surprised and feels less pain.

Each triggering or insertion procedure can be recorded together with time and date stamps with the medical therapy device 450 such as a glucose meter or an insulin pump.

Additional data such as, for example, the insertion location, can also be recorded by the medical therapy device 450 for each triggering or insertion procedure.

The embodiments described herein may comprise a mechanical interface, a non-contact interface, inductive interface or magnetic interface for integrating the trigger device into a medical therapy device 450.

Figure 13:
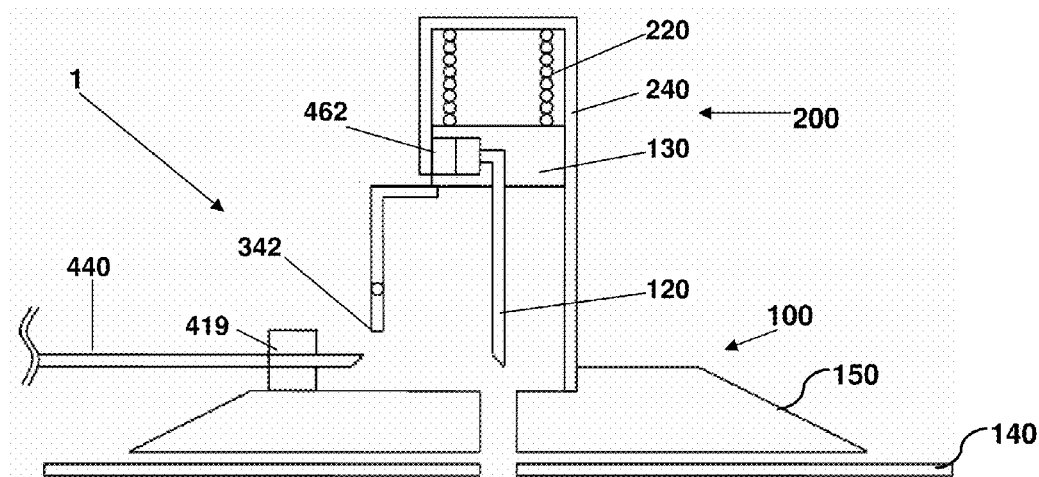
FIG. 13 schematically depicts a cannula system comprising a trigger device integrated in a fluid connector according to one or more embodiments shown and described herein.

FIG. 13 depicts an inserter module 200 that is triggered without using control elements, but rather by connecting a fluid connector 440 to the cannula hub 150.

For example, the embodiment depicted in FIG. 13 may be utilized to administer insulin into a patient. The patient may position a cannula assembly 1 comprising an inserter module 200 on the patient's skin. A fluid connector 440, which has been filled with insulin beforehand, may then be attached to the cannula hub 150. The coupling of the fluid connector 440 to the cannula hub triggers the insertion of the cannula 120. The inserter module 200 then may be decoupled and/or detached from the cannula hub 150. The user can then dispose the inserter module 200 and begin an insulin infusion procedure. In a further embodiment, the inserter module 200 is integrated with the cannula assembly 1 such that the inserter module 200 can be removed after triggering.

The inserter module 200 may be disposable and comprise a biased spring 220. The biased spring 220 can be integrated into the inserter module 200. In the embodiments described herein, the biased spring 220 may be in tension or compression. Furthermore, the energy stores described herein, (e.g., biased spring 220) may be energized and/or discharged automatically and/or manually.

As depicted in FIG. 13, the inserter module 200 has a mechanical locking/releasing mechanism which initially holds the biased spring 220 securely in a tensioned state. Once a fluid connector 440 is connected to the cannula assembly 1, the locking/releasing mechanism is triggered and the cannula 120 is released. The locking/releasing mechanism comprises a release plug 419 that can slide and a tilting device such as a levered retaining hook 342. Linear movement of the fluid connector 440, as it is connected with the cannula hub 150, is converted into a mechanical movement that releases a blocking element. The movement of the blocking element thus causes the biased spring 220 to be discharged. In the embodiment depicted in FIG. 13, a levered retaining hook 342 is the locking/releasing mechanism. The interaction between the release plug 419 and the levered retaining hook 342 causes the levered retaining hook 342 to tilt or pivot. When the levered retaining hook 342 is sufficiently tilted the biased spring 220 is discharged.

In the embodiment depicted in FIG. 13, the trigger device is the fluid connector 440 which may fluidically connect the cannula 120 to an infusion pump. For example, the fluid connector 440 may be connected to the cannula assembly 1 via a tubing connection after the cannula assembly 1 has been attached to the skin of a patient. The fluid connector 440 further comprises a connector cannula for piercing a septum 462.

Referring collectively to FIGS. 13A to 13F, an insertion sequence using the cannula system 10 shown in FIG. 13 is depicted.

Figure 13A:
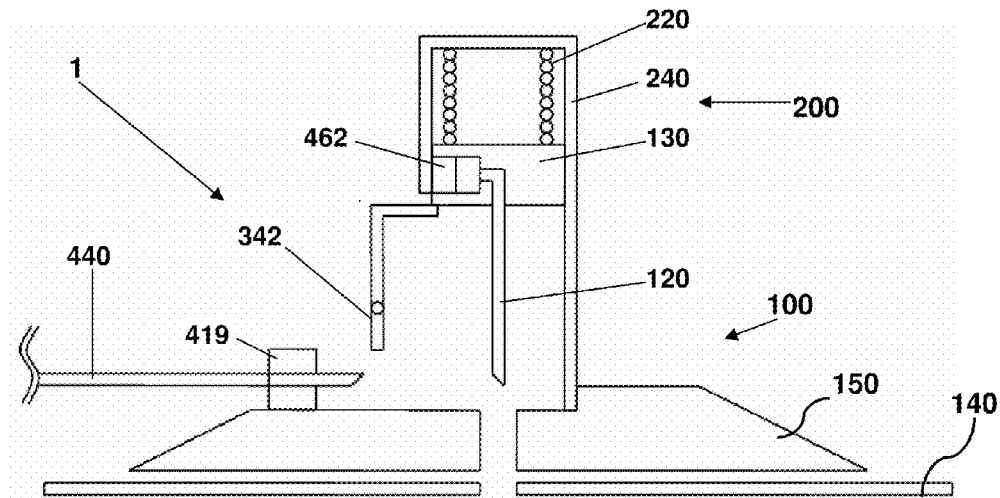
FIGS. 13A to 13E schematically depict an insertion sequence using the cannula system shown in FIG. 13 according to one or more embodiments shown and described herein.

In FIG. 13A, the biased spring 220 is held in a compressed state by a levered retaining hook 342. The levered retaining hook 342 also holds the plunger 130, together with the cannula 120, in a pre-operational (retracted) state. The fluid connector 440 is not engaged with the cannula assembly 1. The release plug 419 of the fluid connector 440 is moved linearly (e.g., to the right) and comes into contact with the levered retaining hook 342.

Figure 13B:
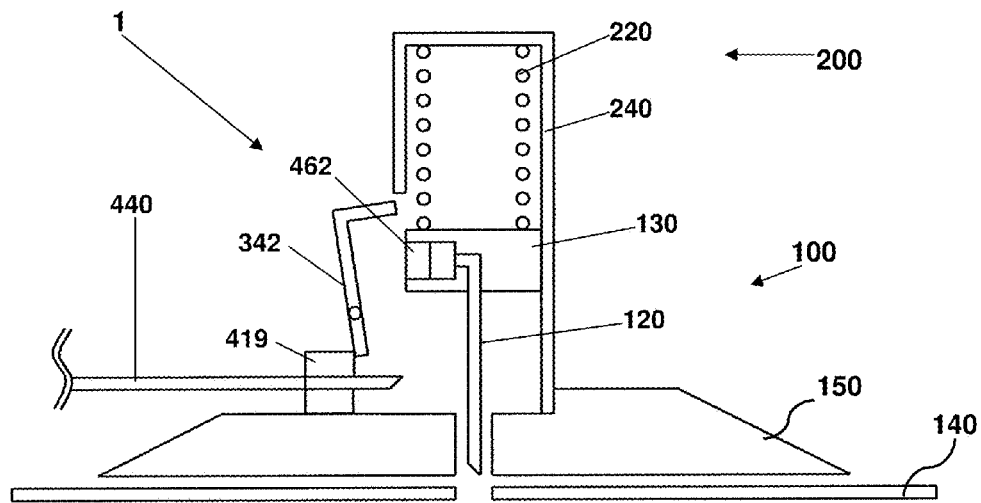

In FIG. 13B, the movement of the fluid connector 440 is depicted. The fluid connector 440 causes the levered retaining hook 342 to be levered in a counter-clockwise direction about its levering point. The engagement between the levered retaining hook 342 and the plunger 130 is released. Accordingly, the plunger 130 together with the cannula 120 is moved downwards by the biased spring 220.

Figure 13C:
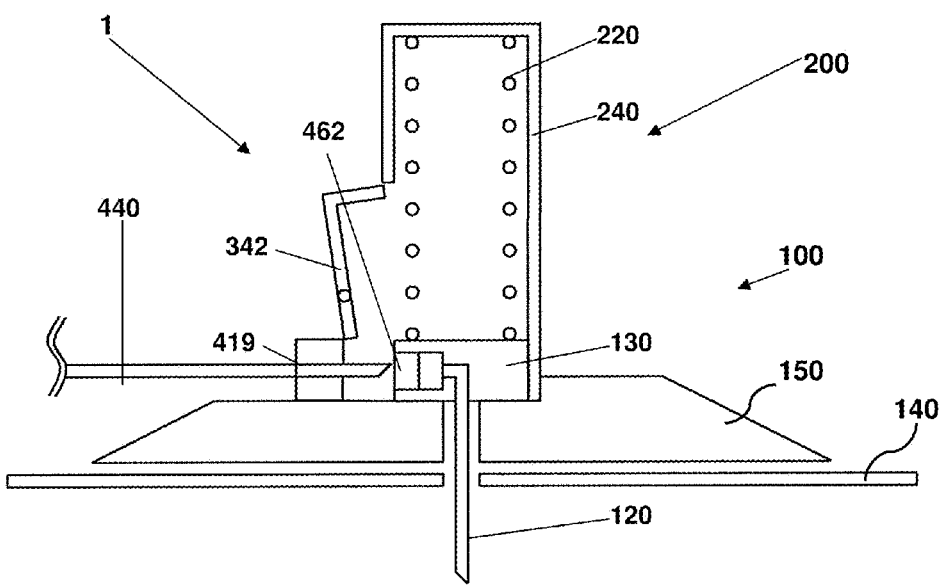

Referring now to FIG. 13C, the plunger 130 comes into contact with the cannula hub 150, and the cannula 120 is in the operational state. The plunger 130 comprises a septum 462 that is integrated for fluidically connecting the cannula 120. In the operational state, the septum 462 is aligned with the fluid connector 440 and the cannula 120, and the biased spring 220 is in an end position (e.g., the biased spring is relaxed). The cannula 120 is secured on the cannula hub 150 by means of a snapping mechanism (not depicted).

Figure 13D:
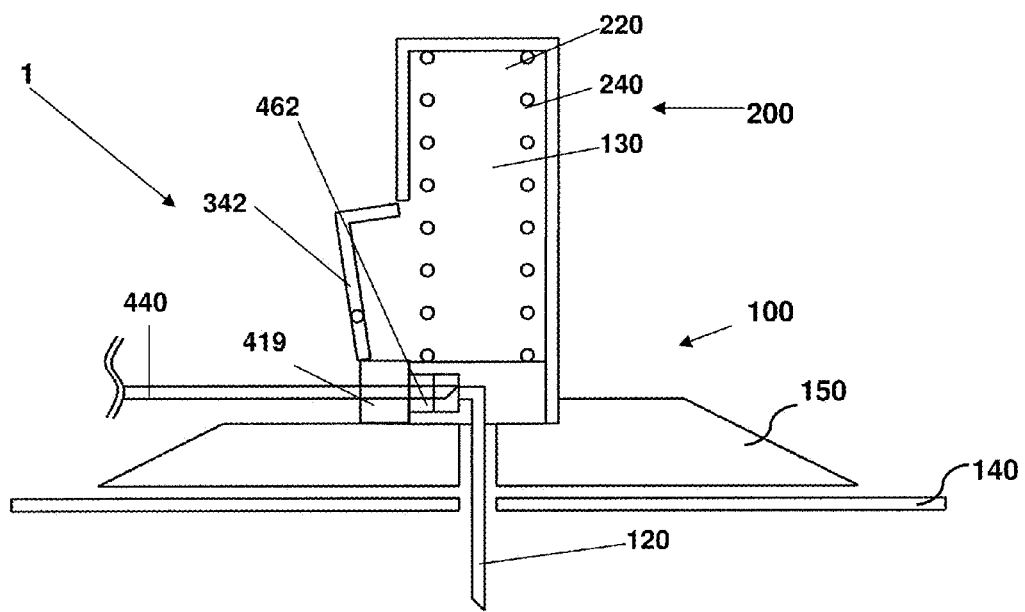

In FIG. 13D, the linear movement of the fluid connector 440 is depicted. The connector cannula pierces the septum 462 and establishes a fluidic connection between the fluid connector 440 and the cannula 120 for infusion. The fluid connector 440 and the cannula hub 150 may engage via a latching mechanism (not depicted).

Figure 13E:
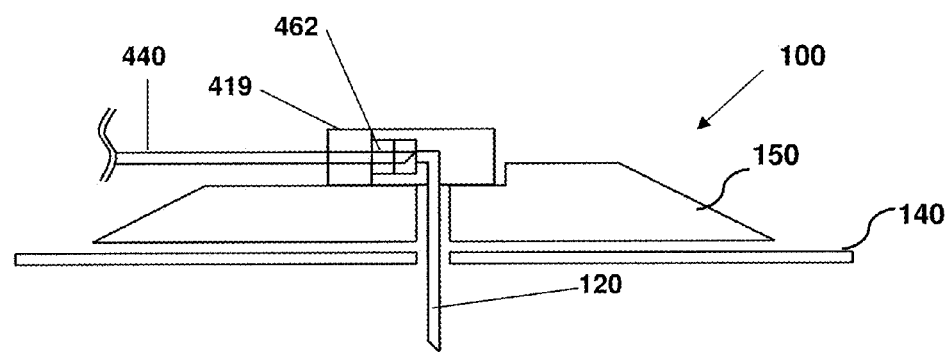

In FIG. 13E, the cannula module 100 is depicted with the inserter module 200 removed. Upon removal of the inserter module 200, the delivery of insulin can be started.

In the embodiments described herein the cannula 120 may be a hollow steel needle with a pointed tip. The cannula 120 may also be a flexible tube. Specifically, the flexible tube may be mechanically supported during insertion by a guiding needle. In embodiments in which a guiding needle is provided, the guiding needle may be retracted once insertion is complete manually or mechanically (e.g., by a second spring).

FIGS. 14 to 17 depict a cannula system 10 in which the cannula assembly is triggered by the flow of a medical product or liquid such as insulin into the activation mechanism.

A priming procedure may be performed. In one embodiment, the fluid connector 440 and the connection tube to the pump are filled with fluid. The cannula hub 150 comprising an inserter module 200 is attached to the fluid connector 440 and the connection tube. Individual insulin dose amount may be set such that when the cannula assembly 1 is activated an insulin pump dispenses insulin. For example, a user may place the cannula assembly 1 onto the skin of a patient. An "Insert" function may be activated on the insulin pump and the desired individual insulin dose may be set. A few seconds after activating the "Insert" function, the cannula 120 is inserted. It is noted that the individual insulin dose amount may be set before or after insertion of the cannula 120. Insulin pumps are typically pre-programmed such that the pump merely has to be started in order to initiate insulin dispensation, i.e., performed automatically at the end of the priming procedure.

Figure 14A:
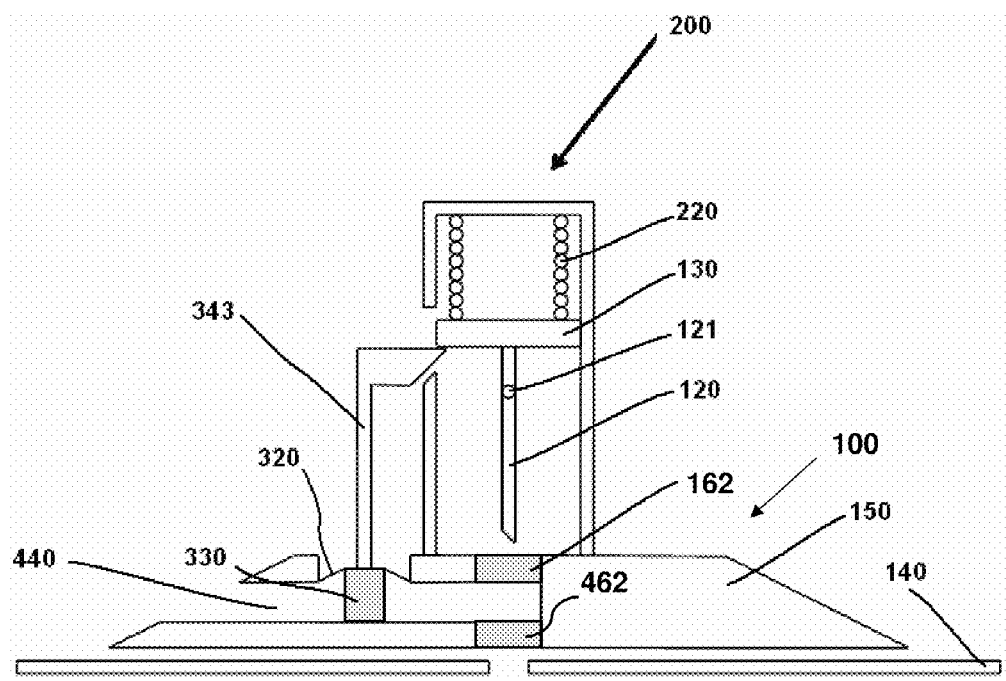
FIG. 14A schematically depicts a cannula system in a pre-operational state, wherein triggering is effected by a fluid or liquid acting on a spongy element according to one or more embodiments shown and described herein.
Figure 14B:
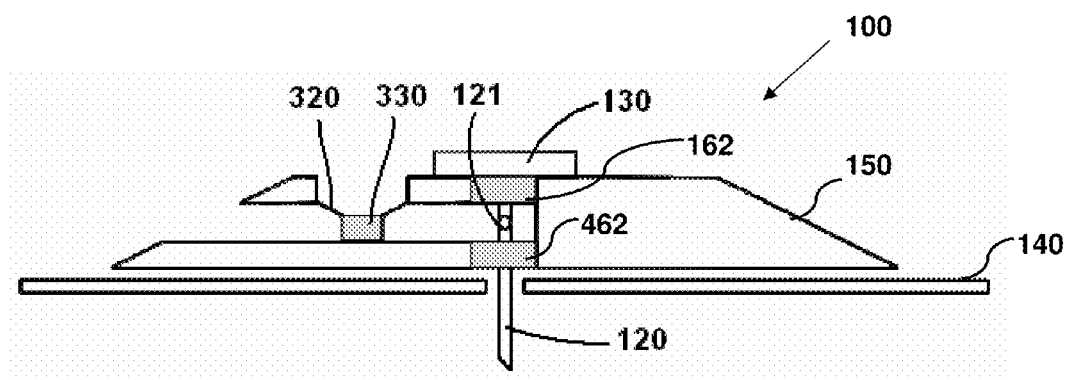
FIG. 14B schematically depicts the cannula system of FIG. 14A in an operational state according to one or more embodiments shown and described herein.

FIGS. 14A and 14B depict an embodiment in which the cannula assembly 1 is triggered by a fluid acting on the activation mechanism (a spongy element 330). An inserter module 200 comprises a biased spring 220. FIG. 14A depicts a pre-operational state of the cannula 120, and FIG. 14B depicts an operational state of the cannula 120.

In the depicted embodiment, a retaining hook 343 is laterally provided and holds the biased spring 220 in a biased state. Inserting the fluid connector 440 levers the retaining hook 343, and the cannula 120 is then injected. The fluid connector 440 also locks the cannula 120 in place.

When fluid such as insulin is supplied, the fluid acts on the spongy element 330. The spongy element 330 becomes soft and a biased elastic element 320 such as, for example, a flexible seal made of a material such as silicone rubber, is inverted. The inversion triggers the activation or insertion mechanism. The retaining hook 343 and the inserter body 240 are chamfered. The inserter body bends the retaining hook 343 (to the left in FIG. 14A) and allows the plunger 130 to move downwards and pass the retaining hook 343 without being blocked.

The cannula assembly 1 may be integral with the inserter module 200 and placed on an administration cite such as the skin of a patient. The fluid connector 440, which has been filled with insulin beforehand, may be attached to the cannula hub 150. The insulin delivery device or pump may be activated to start insulin flow. The insulin flow triggers the insertion of the cannula 120. After the insertion of the cannula 120, the inserter module 200 can be decoupled from the cannula hub 150. The inserter module 200 can be disposed at the start of an insulin infusion procedure.

In practice, the priming procedure can be carried out in three steps: (i) the tubing and the fluid connector 440 are primed, in a detached state, in a first priming step; (ii) the fluid connector 440 is attached; (iii) a second priming procedure is carried out in order to fill the cannula with insulin e.g. after activating the "Insert" function of the insulin pump. Only in step (iii) is the spongy element 330 wetted and the insertion of the cannula 120 triggered. The amount of insulin employed in the second priming procedure should not exceed the amount needed to fill the cannula, in order to prevent additional insulin being unintentionally administered to the patient.

In this embodiment, the insertion of the cannula 120 is triggered by the insulin which flows into the cannula assembly 1 from the insulin pump, wherein the insulin pump serves as the trigger device.

In the pre-operational state, the biased spring 220 is held in a compressed state by a retaining hook 343, as described above. The retaining hook 343 is supported by the biased elastic element 320 connected to the spongy element 330 in the fluid connector 440. When insulin flows into the fluid connector 440 of the cannula module 100, the spongy element 330 is structurally weakened such that it can no longer support the biased elastic element 320. Accordingly, the spongy element 330 causes the biased elastic element 320 to change its state, such that the engagement between the plunger 130 and the retaining hook 343 is released.

Figure 15A:
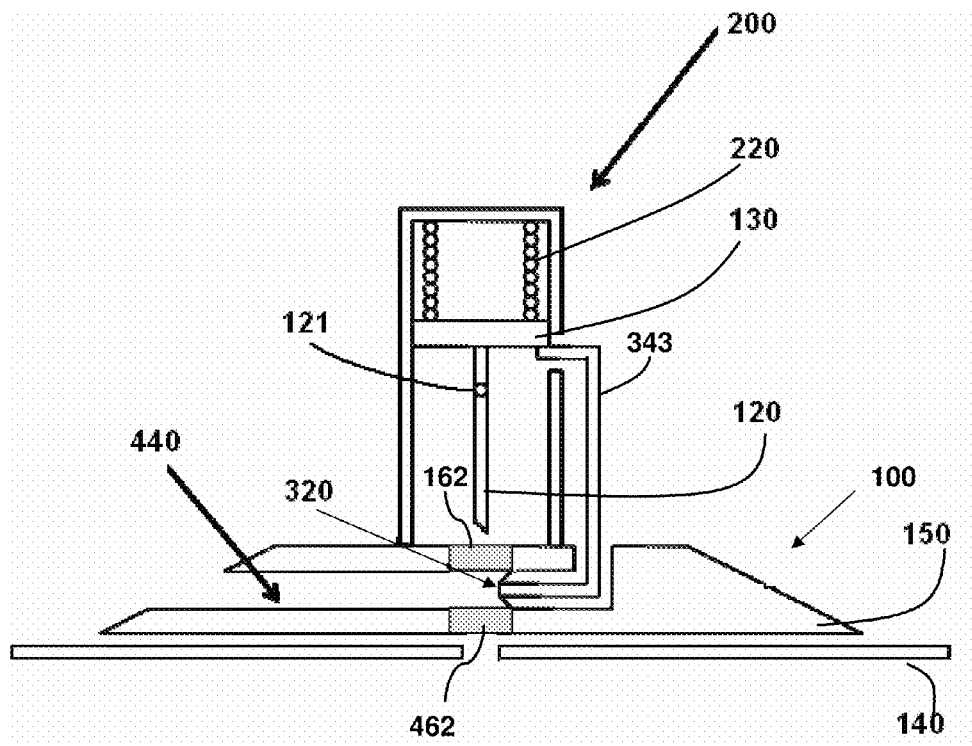
FIG. 15A schematically depicts a cannula system in a pre-operational state, wherein triggering is effected by a fluid or liquid acting on an elastic element according to one or more embodiments shown and described herein.
Figure 15B:
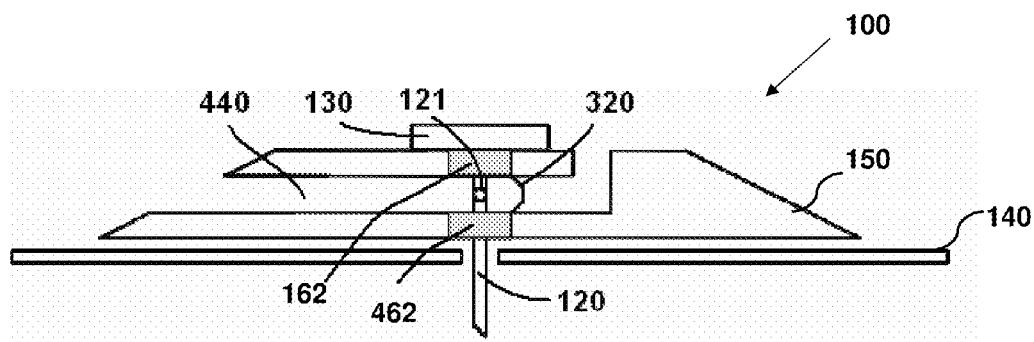
FIG. 15B schematically depicts the cannula system of FIG. 15A in an operational state according to one or more embodiments shown and described herein.

FIGS. 15A and 15B depicts another embodiment wherein the cannula assembly 1 is triggered by a fluid or liquid acting on a biased elastic element 320 such as a bistable elastic element. Once insulin has been transferred into the cannula hub 150 and a certain pressure has accumulated, the biased elastic element 320 is inverted outwards and triggers the inserter module 200. FIG. 15A depicts the pre-operational state of the cannula 120, and FIG. 15B depicts the operational state of the cannula 120.

FIGS. 16 and 17 depict additional embodiments wherein the cannula assembly 1 is triggered by a fluid or liquid acting on a shiftable plug 365. For example, when insulin is transferred into the cannula hub 150, the shiftable plug 365 is moved and triggers the inserter module 200. The triggering releases the lock on the biased spring 220, and moves the cannula 120. In one embodiment, the quantity of insulin which is transferred in the course of the "Insert" function corresponds to the filling volume of the fluid channel and cannula 120.

Figure 16A:
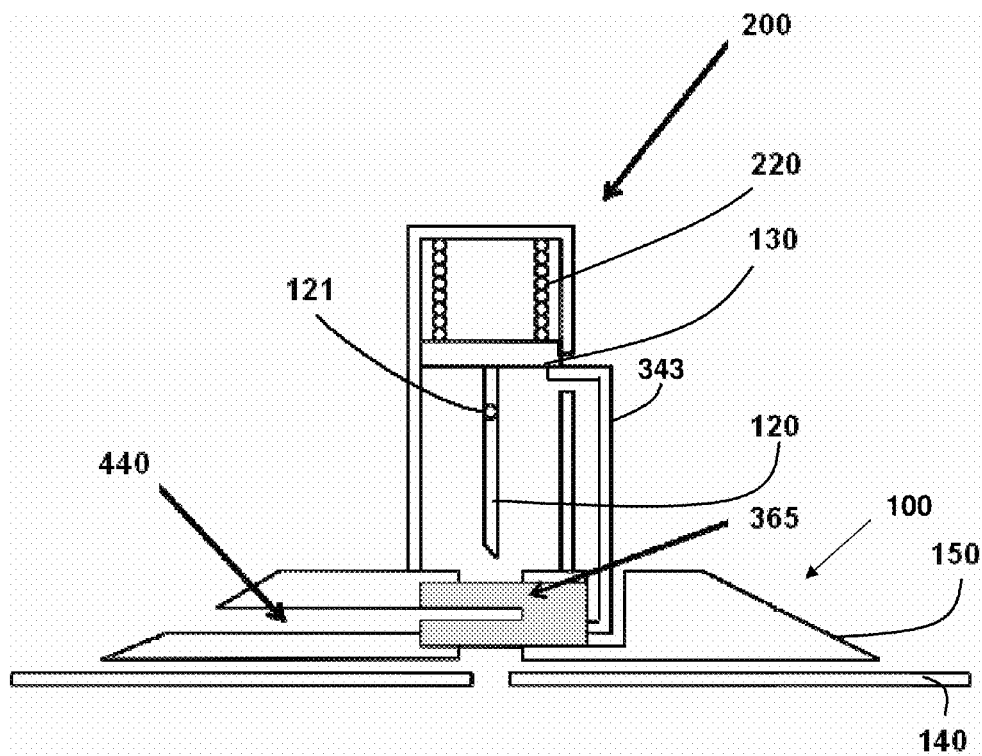
FIG. 16A schematically depicts a cannula system in a pre-operational state, wherein triggering is effected by a fluid or liquid acting on a shiftable plug according to one or more embodiments shown and described herein.
Figure 16B:
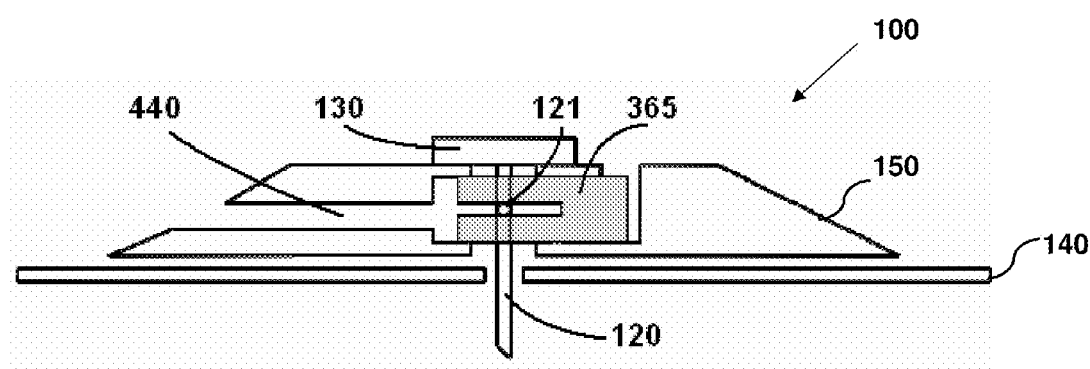
FIG. 16B schematically depicts the cannula system of FIG. 16A in an operational state according to one or more embodiments shown and described herein.
Figure 17A:
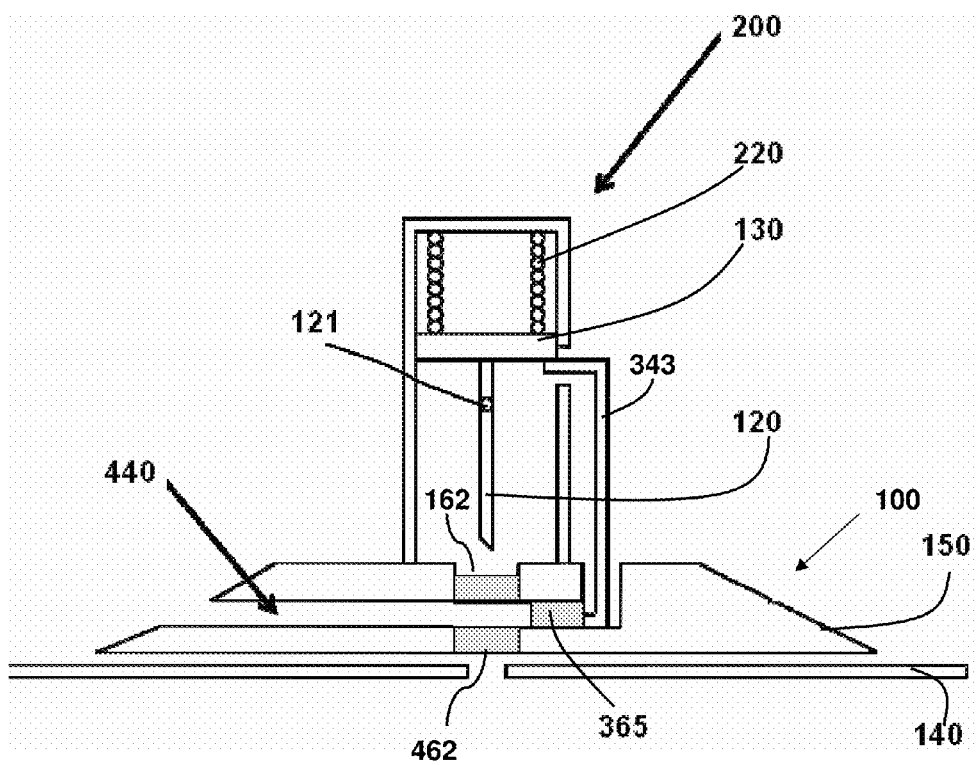
FIG. 17A schematically depicts a cannula system in a pre-operational state, wherein triggering is effected by a fluid or liquid acting on a shiftable plug according to one or more embodiments shown and described herein.
Figure 17B:
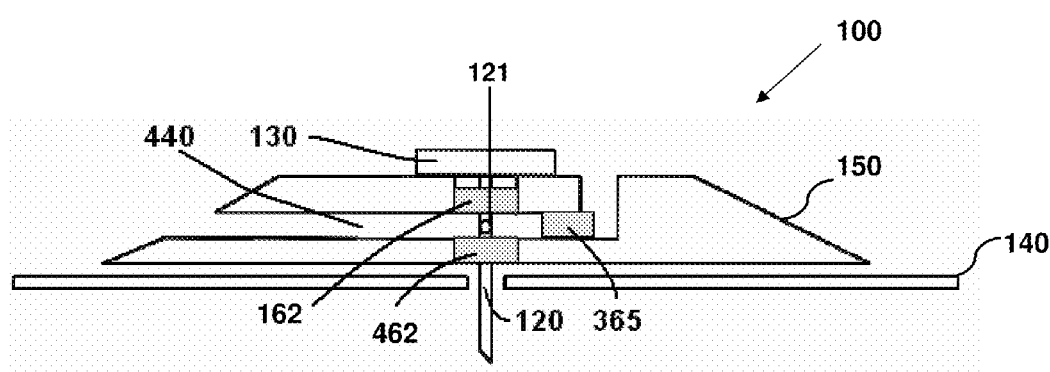
FIG. 17B schematically depicts the cannula system of FIG. 17A in an operational state according to one or more embodiments shown and described herein.

FIGS. 16A and 17A depict a pre-operational state of the cannula 120, and FIGS. 16B and 17B depict the operational state of the cannula 120.

As depicted in FIGS. 14 to 17, embodiments of the cannula 120 comprise a lateral opening 121 which in the operational state of the cannula 120 is positioned so as to be in fluid communication with the fluid connector 440. When the lateral opening 121 is in fluid communication with the fluid connector 440, fluid or liquid can flow through the fluid connector 440, via the lateral opening 121 into the cannula 120.

It will be apparent to those skilled in the art that various modifications and variations can be made to the embodiments described herein without departing from the spirit and the scope of the claimed subject matter. Thus it is intended that the specification cover the modifications and variations of the various embodiments described herein provided such modifications and variations come within the scope of the appended claims and their equivalents.

What is claimed is:

1. A cannula assembly for use with a medical therapy device having a trigger device comprising:
    a cannula module comprising:
        a skin-contacting surface for placing on an outer surface; and
        a cannula having a pre-operational state in which the cannula is retracted with respect to the skin-contacting surface, and an operational state in which the cannula projects beyond the skin-contacting surface;
    an inserter module coupled to the cannula module in the pre-operational state, the inserter module comprising:
        an inserter body having a bearing element formed thereon with an exterior surface and an interior surface;
        a plunger axially fixed to the cannula;
        an energy store on a first side is axially fixed on the interior surface of the bearing element and on an opposite side removably fixed to the plunger, the energy store having stored potential energy wherein when the energy store is at least partially discharged, the stored potential energy is transformed to kinetic energy that moves the cannula from the pre-operational state to the operational state; and
        an activation mechanism triggerable from outside the cannula assembly with the trigger device, the activation mechanism comprising a blocking element disposed along the exterior surface of the bearing element forming a trigger interface, wherein the activation mechanism prevents the energy store from being discharged before it is triggered by the trigger device, and enables the energy store to be discharge after it is triggered by the trigger device to force the cannula from the pre-operational state into the operational state.

2. The cannula assembly according to claim 1, wherein the inserter module is releasably coupled to the cannula module.

3. The cannula assembly according to claim 1, wherein
    the activation mechanism further comprises a retaining element, such that the blocking element is releasably attached to the retaining element and prevents the energy store from being discharged;
    the blocking element is removable from the retaining element by an activating effect, which causes the energy store to be at least partially discharged; and
    the activation mechanism is triggered by moving the blocking element.

4. The cannula assembly according to claim 1 wherein the blocking element comprises a box-shaped cap releasably engaged with the bearing element.

5. The cannula assembly according to claim 3 wherein the activation mechanism is releasably coupled to the exterior surface of the bearing element extending through an opening of the inserter body and releasably coupled to the plunger.

6. The cannula assembly according to claim 3 wherein the retaining element comprises a pivoting hook releasably coupled to the plunger.

7. The cannula assembly according to claim 1 wherein the energy store is a biased spring.

* * * * *

UNITED STATES PATENT AND TRADEMARK OFFICE
CERTIFICATE OF CORRECTION

PATENT NO. : 8,475,410 B2
APPLICATION NO. : 12/951151
DATED : July 2, 2013
INVENTOR(S) : Heiner Kaufmann et al.

It is certified that error appears in the above-identified patent and that said Letters Patent is hereby corrected as shown below:

On the Title Page

Item (75) Inventors: "Simon Scheuer, Bern (CH)" should read --Simon Scheurer, Bern (CH);--;

Item (73) Assignee: "Roche Diagnostics International AG, Steinhausen (CH)" should read
--Roche Diagnostics International AG, Rotkreuz (CH)--;

Item (57) ABSTRACT
"According to one embodiment, a cannula assembly may include a cannula module and an inserter module. In the pre-operational state the cannula is retracted with respect to the skin-contacting surface. In operational state the cannula projects beyond the skin-contacting surface. The inserter module may include an energy store and an activation mechanism. When the energy store is at least partially discharged, the stored potential energy is transformed to kinetic energy that moves the cannula from the pre-operational state to the operational state. The activation mechanism is triggerable from outside the cannula assembly with a trigger device. The activation mechanism prevents the energy store from being discharged before it is triggered by the trigger device, and enables the energy store to be discharge after it is triggered by the trigger device to force the cannula from the pre-operational state into the operational state."

should read

Item (57) ABSTRACT
--According to one embodiment, a cannula assembly may include a cannula module and an inserter module. In the pre-operational state the cannula is retracted with respect to the skin-contacting surface. In operational state the cannula projects beyond the skin-contacting surface. The inserter module may include an energy store and an activation mechanism. When the energy store is at least partially discharged, the stored potential energy is transformed to kinetic energy that moves the cannula from the pre-operational state to the operational state. The activation mechanism is triggerable from outside the cannula assembly with a trigger device. The activation mechanism prevents the energy store from Signed and Sealed this
Twenty-fourth Day of June, 2014

Michelle K. Lee
*Deputy Director of the United States Patent and Trademark Office* being discharged before it is triggered by the trigger device, and enables the energy store to be discharged after it is triggered by the trigger device to force the cannula from the pre-operational state into the operational state.--;

In the Specification

Col. 1, Line 57, "at least one piercing member of the insertion set thorough the" should read
--at least one piercing member of the insertion set through the--;

Col. 2, Line 53, "enables the energy store to be discharge after it is triggered by" should read
--enables the energy store to be discharged after it is triggered by--;

Col. 10, Line 18, "mechanism," should read --mechanism.--;

Col. 11, Line 25-26, "A trigger device may comprise trigger interface of the having an actuator. The trigger device can be designed to" should read --A trigger device may comprise a trigger interface having an actuator. The trigger device can be designed to--;

Col. 14, Line 5, "200 maybe releasably coupled to the cannula module 100 in" should read
--200 may be releasably coupled to the cannula module 100 in--;

Col. 15, Line 48, "cannula 120 maybe triggered only if both buttons are pushed." should read
--cannula 120 may be triggered only if both buttons are pushed.--;

Col. 20, Line 14, "module 200 and placed on an administration cite such as the" should read
--module 200 and placed on an administration site such as the--; and In the Claims Col. 22, Claim 1, Line 12, "device, and enables the energy store to be discharge" should read
--device, and enables the energy store to be discharged--.